(12) United States Patent
Svoboda et al.

(10) Patent No.: US 11,045,124 B2
(45) Date of Patent: Jun. 29, 2021

(54) ELECTROCHEMICAL SENSORS AND METHODS FOR MAKING ELECTROCHEMICAL SENSORS USING ADVANCED PRINTING TECHNOLOGY

(71) Applicant: PEPEX BIOMEDICAL, INC., St. Louis, MO (US)

(72) Inventors: Vojtech Svoboda, Atlanta, GA (US); James L. Say, Breckenridge, CO (US); Stephen L. Pohl, Prescott, WI (US)

(73) Assignee: PEPEX BIOMEDICAL, INC., St. Louis, MO (US)

( * ) Notice: Subject to any disclaimer, the term of this patent is extended or adjusted under 35 U.S.C. 154(b) by 615 days.

(21) Appl. No.: 15/315,973

(22) PCT Filed: Jun. 4, 2015

(86) PCT No.: PCT/US2015/034210
§ 371 (c)(1),
(2) Date: Dec. 2, 2016

(87) PCT Pub. No.: WO2015/187959
PCT Pub. Date: Dec. 10, 2015

(65) Prior Publication Data
US 2017/0095187 A1    Apr. 6, 2017

Related U.S. Application Data

(60) Provisional application No. 62/007,694, filed on Jun. 4, 2014, provisional application No. 62/036,966, filed on Aug. 13, 2014.

(51) Int. Cl.
| | | |
|---|---|---|
| *A61B 5/1486* | (2006.01) |
| *B41M 3/00* | (2006.01) |
| *A61B 5/15* | (2006.01) |
| *A61B 5/145* | (2006.01) |
| *G01N 27/327* | (2006.01) |

(52) U.S. Cl.
CPC ...... *A61B 5/14865* (2013.01); *A61B 5/14532* (2013.01); *A61B 5/14546* (2013.01);
(Continued)

(58) Field of Classification Search
CPC ............ A61B 5/14865; A61B 5/14532; A61B 5/14546; A61B 5/150022;
(Continued)

(56) References Cited

U.S. PATENT DOCUMENTS

| | | |
|---|---|---|
| 1,454,224 A | 5/1923 | Schmidt |
| 2,291,720 A | 8/1942 | Hukle |
| (Continued) | | |

FOREIGN PATENT DOCUMENTS

| | | |
|---|---|---|
| CA | 2050677 C | 3/1992 |
| DE | 4105222 A1 | 8/1992 |
| (Continued) | | |

OTHER PUBLICATIONS

European Search Report for 09826755.2 dated Oct. 5, 2012.
(Continued)

*Primary Examiner* — Christian Jang
*Assistant Examiner* — Mitchell E Alter
(74) *Attorney, Agent, or Firm* — Merchant & Gould P.C.

(57) ABSTRACT

A sensor can be manufactured by printing a working electrode onto a substrate using aerosol jet printing. Sensing chemistry (e.g., enzyme-based ink that including detection chemistry) also can be printed onto the working electrode using aerosol jet printing. A reference electrode also can be printed on the substrate at a position spaced along the substrate from the working electrode. In certain examples, the substrate can be positioned within a lumen of a skin piercing member of a sensor module.

21 Claims, 14 Drawing Sheets

(52) U.S. Cl.
CPC .. *A61B 5/150022* (2013.01); *A61B 5/150213* (2013.01); *A61B 5/150389* (2013.01); *A61B 5/150503* (2013.01); *A61B 5/150755* (2013.01); *B41M 3/006* (2013.01); *G01N 27/3271* (2013.01)

(58) Field of Classification Search
CPC ........ A61B 5/150213; A61B 5/150389; A61B 5/150503; A61B 5/150755; B41M 3/006; G01N 27/3271
USPC ......................................... 600/309, 345–366
See application file for complete search history.

(56) References Cited

U.S. PATENT DOCUMENTS

| | | |
|---|---|---|
| 3,170,968 A | 2/1965 | Rokunohe et al. |
| 3,766,910 A | 10/1973 | Lake |
| 3,823,035 A | 7/1974 | Sanders |
| 4,008,717 A | 2/1977 | Kowarski |
| 4,073,974 A | 2/1978 | Albarino et al. |
| 4,224,125 A | 9/1980 | Nakamura et al. |
| 4,255,487 A | 3/1981 | Sanders |
| 4,321,057 A | 3/1982 | Buckles |
| 4,399,099 A | 8/1983 | Buckles |
| 4,439,303 A | 3/1984 | Cocchi |
| 4,545,382 A | 10/1985 | Higgins et al. |
| 4,545,835 A | 10/1985 | Gusack et al. |
| 4,552,840 A | 11/1985 | Riffer |
| 4,573,968 A | 3/1986 | Parker |
| 4,640,821 A | 2/1987 | Mody et al. |
| 4,671,288 A | 6/1987 | Gough |
| 4,704,311 A | 11/1987 | Pickering et al. |
| 4,734,184 A | 3/1988 | Burleigh et al. |
| 4,762,603 A | 8/1988 | Morin |
| 4,805,624 A | 2/1989 | Yao et al. |
| 4,820,399 A | 4/1989 | Klainer et al. |
| 4,824,206 A | 5/1989 | Saxena |
| 4,833,083 A | 7/1989 | Klainer |
| 4,846,548 A | 7/1989 | Klainer |
| 4,880,752 A | 11/1989 | Keck et al. |
| 4,908,115 A | 3/1990 | Morita et al. |
| 4,919,649 A | 4/1990 | Timothy et al. |
| 4,927,516 A | 5/1990 | Yamaguchi et al. |
| 4,945,896 A | 8/1990 | Gade |
| 4,974,929 A | 12/1990 | Curry |
| 4,981,779 A | 1/1991 | Wagner |
| 5,001,054 A | 3/1991 | Wagner |
| 5,002,651 A | 3/1991 | Shaw et al. |
| 5,004,583 A | 4/1991 | Guruswamy et al. |
| RE33,677 E | 8/1991 | Vazirani |
| 5,047,044 A | 9/1991 | Smith et al. |
| 5,112,455 A | 5/1992 | Cozzette et al. |
| 5,131,138 A | 7/1992 | Crouse |
| 5,164,229 A | 11/1992 | Hay et al. |
| 5,165,406 A | 11/1992 | Wong |
| 5,165,407 A | 11/1992 | Wilson et al. |
| 5,171,689 A | 12/1992 | Kawaguri et al. |
| 5,186,808 A | 2/1993 | Yamaguchi et al. |
| 5,205,920 A | 4/1993 | Oyama et al. |
| 5,217,533 A | 6/1993 | Hay et al. |
| 5,220,920 A | 6/1993 | Gharib |
| 5,243,982 A | 9/1993 | Möstl et al. |
| 5,244,636 A | 9/1993 | Walt et al. |
| 5,250,264 A | 10/1993 | Walt et al. |
| 5,262,035 A | 11/1993 | Gregg et al. |
| 5,264,092 A | 11/1993 | Skotheim et al. |
| 5,264,103 A | 11/1993 | Yoshioka et al. |
| 5,264,104 A | 11/1993 | Gregg et al. |
| 5,264,105 A | 11/1993 | Gregg et al. |
| 5,269,891 A | 12/1993 | Colin |
| 5,271,815 A | 12/1993 | Wong |
| 5,271,820 A | 12/1993 | Kinlen et al. |
| 5,277,872 A | 1/1994 | Bankert et al. |
| 5,286,362 A | 2/1994 | Hoenes et al. |
| 5,298,144 A | 3/1994 | Spokane |
| 5,298,741 A | 3/1994 | Walt et al. |
| 5,320,725 A | 6/1994 | Gregg et al. |
| 5,320,814 A | 6/1994 | Walt et al. |
| 5,330,634 A | 7/1994 | Wong et al. |
| 5,356,786 A | 10/1994 | Heller et al. |
| 5,366,527 A | 11/1994 | Amos et al. |
| 5,372,133 A | 12/1994 | Hogen esch |
| D354,347 S | 1/1995 | Knute et al. |
| D354,559 S | 1/1995 | Knute et al. |
| 5,384,028 A | 1/1995 | Ito |
| 5,386,828 A | 2/1995 | Owens et al. |
| 5,395,504 A | 3/1995 | Saurer et al. |
| 5,422,246 A | 6/1995 | Koopal et al. |
| 5,431,174 A | 7/1995 | Knute |
| 5,437,973 A | 8/1995 | Vadgama et al. |
| 5,503,728 A | 4/1996 | Kaneko et al. |
| 5,505,828 A | 4/1996 | Wong et al. |
| 5,512,159 A | 4/1996 | Yoshioka et al. |
| 5,515,848 A | 5/1996 | Corbett et al. |
| 5,543,012 A | 8/1996 | Watson et al. |
| 5,575,403 A | 11/1996 | Charlton et al. |
| 5,591,139 A | 1/1997 | Lin et al. |
| 5,593,852 A | 1/1997 | Heller et al. |
| 5,605,152 A | 2/1997 | Slate et al. |
| 5,609,749 A | 3/1997 | Yamauchi et al. |
| 5,645,710 A | 7/1997 | Shieh |
| 5,656,241 A | 8/1997 | Seifert et al. |
| 5,704,354 A | 1/1998 | Preidel et al. |
| 5,720,924 A | 2/1998 | Eikmeier et al. |
| 5,777,060 A | 7/1998 | Van Antwerp |
| 5,800,350 A * | 9/1998 | Coppleson ........... A61B 5/0059 600/372 |
| 5,810,199 A | 9/1998 | Charlton et al. |
| 5,814,601 A | 9/1998 | Winslow et al. |
| 5,849,415 A | 12/1998 | Shalaby et al. |
| 5,863,800 A | 1/1999 | Eikmeier et al. |
| 5,900,215 A | 5/1999 | Seifert et al. |
| 5,951,764 A | 9/1999 | Hay et al. |
| 5,971,941 A | 10/1999 | Simons et al. |
| 5,972,199 A | 10/1999 | Heller et al. |
| 5,982,959 A | 11/1999 | Hopenfeld |
| 5,997,501 A | 12/1999 | Gross et al. |
| 6,004,818 A | 12/1999 | Freilich et al. |
| 6,036,924 A | 3/2000 | Simons et al. |
| 6,044,665 A | 4/2000 | Lysson et al. |
| 6,048,352 A | 4/2000 | Douglas et al. |
| D424,696 S | 5/2000 | Ray et al. |
| D426,638 S | 6/2000 | Ray et al. |
| 6,071,294 A | 6/2000 | Simons et al. |
| 6,071,391 A | 6/2000 | Gotoh et al. |
| 6,083,710 A | 7/2000 | Heller et al. |
| 6,099,484 A | 8/2000 | Douglas et al. |
| 6,103,033 A | 8/2000 | Say et al. |
| 6,103,199 A | 8/2000 | Bjornson et al. |
| 6,104,940 A | 8/2000 | Watanabe et al. |
| 6,107,083 A | 8/2000 | Collins et al. |
| 6,120,676 A | 9/2000 | Heller et al. |
| 6,143,164 A | 11/2000 | Heller et al. |
| 6,241,863 B1 | 6/2001 | Montbouquette |
| 6,299,757 B1 | 10/2001 | Feldman et al. |
| 6,329,161 B1 | 12/2001 | Heller et al. |
| 6,338,790 B1 | 1/2002 | Feldman et al. |
| 6,349,229 B1 | 2/2002 | Watanabe et al. |
| 6,375,627 B1 * | 4/2002 | Mauze ............... A61B 5/14532 600/309 |
| 6,379,317 B1 | 4/2002 | Kintzig et al. |
| 6,461,496 B1 | 10/2002 | Feldman et al. |
| 6,464,849 B1 | 10/2002 | Say et al. |
| 6,484,045 B1 * | 11/2002 | Holker ............... A61B 5/14865 204/403.01 |
| 6,500,144 B1 * | 12/2002 | Russell ............. A61M 25/0105 600/585 |
| 6,503,381 B1 | 1/2003 | Gotoh et al. |
| 6,560,471 B1 | 5/2003 | Heller et al. |
| 6,561,989 B2 | 5/2003 | Whitson |
| 6,576,101 B1 | 6/2003 | Heller et al. |
| 6,576,102 B1 | 6/2003 | Rappin et al. |
| 6,591,125 B1 | 7/2003 | Buse et al. |

(56) References Cited

U.S. PATENT DOCUMENTS

| | | |
|---|---|---|
| 6,592,745 B1 | 7/2003 | Feldman et al. |
| 6,607,658 B1 | 8/2003 | Heller et al. |
| 6,610,978 B2 | 8/2003 | Yin et al. |
| 6,616,819 B1 | 9/2003 | Liamos et al. |
| 6,618,934 B1 | 9/2003 | Feldman et al. |
| 6,620,112 B2 | 9/2003 | Klitmose |
| 6,676,816 B2 | 1/2004 | Mao et al. |
| 6,706,159 B2 | 3/2004 | Moerman et al. |
| 6,707,554 B1 | 3/2004 | Miltner et al. |
| 6,740,214 B1 | 5/2004 | Dobson et al. |
| 6,749,740 B2 | 6/2004 | Liamos et al. |
| 6,783,502 B2 | 8/2004 | Orloff et al. |
| 6,840,912 B2 | 1/2005 | Kloepfer et al. |
| 6,866,675 B2 | 3/2005 | Perez et al. |
| 6,881,551 B2 | 4/2005 | Heller et al. |
| 6,892,085 B2 | 5/2005 | McIvor et al. |
| 6,893,545 B2 | 5/2005 | Gotoh et al. |
| 6,965,791 B1 | 11/2005 | Hitchcock et al. |
| 7,008,799 B1 | 3/2006 | Zimmer et al. |
| 7,058,437 B2 | 6/2006 | Buse et al. |
| 7,211,437 B2 | 5/2007 | Schabbach et al. |
| 7,264,139 B2 | 9/2007 | Brickwood et al. |
| 7,282,705 B2 | 10/2007 | Brennen |
| 7,299,081 B2 | 11/2007 | Mace et al. |
| 7,322,942 B2 | 1/2008 | Roe |
| 7,335,294 B2 | 2/2008 | Heller et al. |
| 7,344,499 B1 | 3/2008 | Prausnitz et al. |
| 7,378,007 B2 | 5/2008 | Moerman et al. |
| 7,396,334 B2 | 7/2008 | Kuhr et al. |
| 7,585,278 B2 | 9/2009 | Aceti et al. |
| 7,723,099 B2 | 5/2010 | Miller et al. |
| 7,740,581 B2 | 6/2010 | Buse et al. |
| 7,828,749 B2 | 11/2010 | Douglas et al. |
| 7,829,023 B2 | 11/2010 | Burke et al. |
| 7,860,544 B2 | 12/2010 | Say et al. |
| 8,229,535 B2 | 7/2012 | Mensinger et al. |
| 8,296,918 B2 | 10/2012 | Alden et al. |
| 8,702,932 B2 * | 4/2014 | Say .................. G01N 27/327 |
| | | 204/403.1 |
| 8,828,200 B2 | 9/2014 | Marquant et al. |
| 9,044,178 B2 * | 6/2015 | Say .................. A61B 5/14532 |
| 9,459,228 B2 * | 10/2016 | Say .................. G01N 27/327 |
| 2002/0040208 A1 | 4/2002 | Flaherty et al. |
| 2002/0098124 A1 | 7/2002 | Bentsen et al. |
| 2003/0083686 A1 | 5/2003 | Freeman et al. |
| 2003/0211619 A1 | 11/2003 | Olson et al. |
| 2003/0212346 A1 | 11/2003 | Yuzhakov et al. |
| 2004/0087033 A1 | 5/2004 | Schembri |
| 2004/0102717 A1 | 5/2004 | Qi |
| 2004/0236251 A1 | 11/2004 | Roe et al. |
| 2005/0023137 A1 | 2/2005 | Bhullar et al. |
| 2005/0067737 A1 | 3/2005 | Rappin et al. |
| 2005/0089944 A1 | 4/2005 | Shieh et al. |
| 2005/0143635 A1 | 6/2005 | Kamath et al. |
| 2005/0196747 A1 | 9/2005 | Stiene |
| 2005/0197548 A1 | 9/2005 | Dietiker |
| 2005/0238537 A1 | 10/2005 | Say et al. |
| 2006/0241517 A1 | 10/2006 | Fowler et al. |
| 2007/0027385 A1 * | 2/2007 | Brister .................. A61B 5/1495 |
| | | 600/365 |
| 2007/0093704 A1 | 4/2007 | Brister |
| 2007/0123803 A1 | 5/2007 | Fujiwara et al. |
| 2007/0149897 A1 | 6/2007 | Ghesquiere et al. |
| 2007/0197889 A1 | 8/2007 | Brister |
| 2007/0199818 A1 | 8/2007 | Petyt et al. |
| 2007/0218281 A1 | 9/2007 | Demir et al. |
| 2008/0017645 A1 | 1/2008 | Garagiola |
| 2008/0097546 A1 | 4/2008 | Powers et al. |
| 2008/0167578 A1 | 7/2008 | Bryer et al. |
| 2008/0319314 A1 | 12/2008 | Hill et al. |
| 2009/0021901 A1 | 1/2009 | Stothers |
| 2009/0032760 A1 | 2/2009 | Muscatell |
| 2009/0062767 A1 * | 3/2009 | Van Antwerp ....... A61B 5/6846 |
| | | 604/504 |
| 2009/0069654 A1 | 3/2009 | Yasuzawa et al. |
| 2009/0178923 A1 * | 7/2009 | Marquant .......... A61B 5/14532 |
| | | 204/403.01 |
| 2009/0257917 A1 | 10/2009 | Nakamura et al. |
| 2010/0018869 A1 | 1/2010 | Feldman et al. |
| 2010/0018871 A1 | 1/2010 | Feldman et al. |
| 2010/0051479 A1 | 3/2010 | Heller et al. |
| 2010/0059372 A1 | 3/2010 | Heller et al. |
| 2010/0059373 A1 | 3/2010 | Heller et al. |
| 2010/0072063 A1 | 3/2010 | Heller et al. |
| 2010/0072064 A1 | 3/2010 | Heller et al. |
| 2010/0326842 A1 | 12/2010 | Mazza et al. |
| 2011/0028815 A1 | 2/2011 | Simpson et al. |
| 2011/0086373 A1 | 4/2011 | Wallace-Davis et al. |
| 2011/0172559 A1 | 7/2011 | Fei et al. |
| 2011/0180405 A1 | 7/2011 | Chinnayelka et al. |
| 2011/0203941 A1 | 8/2011 | Say |
| 2011/0265944 A1 | 11/2011 | Say |
| 2011/0266149 A1 | 11/2011 | Say |
| 2011/0270061 A1 | 11/2011 | Say |
| 2012/0046533 A1 | 2/2012 | Voskanyan et al. |
| 2012/0291254 A1 | 11/2012 | Say |
| 2014/0318988 A1 | 10/2014 | Say |
| 2015/0313521 A1 | 11/2015 | Say |
| 2017/0067845 A1 * | 3/2017 | Say .................... G01N 27/3275 |

FOREIGN PATENT DOCUMENTS

| | | |
|---|---|---|
| DE | 20009392 U1 | 11/2000 |
| DE | 10112384 A1 | 9/2002 |
| DE | 102004060742 A1 | 7/2006 |
| EP | 0 256 415 A2 | 2/1988 |
| EP | 0 327 658 A1 | 8/1989 |
| EP | 0 409 033 A2 | 1/1991 |
| EP | 0 420 296 A1 | 4/1991 |
| EP | 0 567 725 A1 | 11/1993 |
| EP | 0 592 805 A2 | 4/1994 |
| EP | 0 710 835 A2 | 5/1996 |
| EP | 0 792 620 A2 | 9/1997 |
| EP | 0 965 301 A1 | 12/1999 |
| EP | 1 462 775 B1 | 12/2007 |
| JP | 64-3552 | 1/1989 |
| JP | 1-153952 | 6/1989 |
| JP | 1-263537 | 10/1989 |
| JP | 4-279854 | 10/1992 |
| JP | 6-174946 | 6/1994 |
| JP | 8-107890 | 4/1996 |
| JP | 3457964 B2 | 10/2003 |
| JP | 2007-202632 | 8/2007 |
| WO | WO 89/07139 | 8/1989 |
| WO | WO 90/10861 A1 | 9/1990 |
| WO | WO 91/15993 | 10/1991 |
| WO | WO 94/10553 | 5/1994 |
| WO | WO 96/06947 | 3/1996 |
| WO | WO 96/22730 | 8/1996 |
| WO | WO 96/39616 | 12/1996 |
| WO | WO 97/15827 | 5/1997 |
| WO | WO 00/35340 | 6/2000 |
| WO | WO 2005/051183 A1 | 6/2005 |
| WO | 2007/037970 A1 | 4/2007 |
| WO | WO 2007/091633 A1 | 8/2007 |
| WO | WO 2008/017645 A1 | 2/2008 |
| WO | WO 2008/118919 A1 | 10/2008 |
| WO | WO 2009/032760 A2 | 3/2009 |
| WO | WO 2009/051901 A2 | 4/2009 |
| WO | WO 2010/056869 A2 | 5/2010 |
| WO | WO 2010/056876 A2 | 5/2010 |
| WO | WO 2010/056878 A2 | 5/2010 |
| WO | 2011/003039 A2 | 1/2011 |
| WO | WO 2012/043051 A1 | 4/2012 |
| WO | WO 2012/106060 A2 | 8/2012 |
| WO | 2014/025430 A2 | 2/2014 |

OTHER PUBLICATIONS

Gough et al., "Short-term In Vivo operation of a glucose sensor," *A.S.A.I.O. Transactions* (1986) 32 (1): 148-150. XP000009622.

International Search Report and Written Opinion for PCT/US2008/074649 dated Apr. 20, 2009.

(56) References Cited

OTHER PUBLICATIONS

International Search Report and Written Opinion for PCT/US2008/074644 dated May 14, 2009.
International Search Report and Written Opinion for PCT/US2009/064216 dated May 3, 2010.
International Search Report and Written Opinion for PCT/US2009/064225 dated May 4, 2010.
International Search Report and Written Opinion for PCT/US2009/064228 dated Jul. 1, 2010.
Jaraba et al., "NADH amperometric sensor based on poly(3-methylthiophene)-coated cylindrical carbon fiber microelectrodes: application to the enzymatic determination of L-lactate," *Electrochimica Acta*. (1998) 43 (23): 3555-3565.
Netchiporouk et al., "Properties of carbon fibre microelectrodes as a basis for enzyme biosensors," *Analytica Chimica Acta* (1995) 303: 275-283.
Sakslund et al, "Analysis of the factors determining the sensitivity of a miniaturized glucose biosensor made by codeposition of palladium and glucose oxidase onto an 8 μm carbon filter," *Journal of Electroanalytical Chemistry* (1996) 402: 149-160.
Sakslund et al., "Development and evaluation of glucose microsensors based on electrochemical codeposition of ruthenium and glucose oxidase onto carbon fiber microelectrodes," *Journal of Electroanalytical Chemistry* (1995) 397: 149-155.
International Search Report and Written Opinion for PCT/US2013/072846 dated Mar. 26, 2014.
European Search Report for European Patent Application No. 13860026.7, dated Dec. 23, 2016.
Marinov et al., "Direct-WriteVapor Sensors on FR4 Plastic Substrates", IEEE Sensors Journal, IEEE Service Center, 7(6):937-944 (2007).
Hoey et al., "A Review on Aerosol-Based Direct-Write and Its Applications for Microelectronics", Journal of Nanotechnology, 26(6):887-22 (2012).
Young et al., "Future Opportunities for Advancing Glucose Test Device Electronics",Journal of diabetes science and A 1-15 technology:1077-1086 (2011).
Zhang, "Printed Electronics: Manufacturing Technologies and Applications Presentation Outline Introduction to Georgia Tech Manufacturing Institute Overview of printed electronics technology and applications Aerosol Jet Printing (AJP) process Application case studies":18-26 (2014).
Search Report for European Patent Application No. 15802478.6, dated Feb. 22, 2018.
International Search Report and Written Opinion for PCT/US2015/034210, dated Sep. 8, 2015.

\* cited by examiner

ELECTROCHEMICAL SENSORS AND METHODS FOR MAKING ELECTROCHEMICAL SENSORS USING ADVANCED PRINTING TECHNOLOGY

CROSS-REFERENCE TO RELATED APPLICATION

The present application is a National Stage Application of International Patent Application No. PCT/US2015/034210, filed Jun. 4, 2015, which claims the benefit of U.S. Provisional Patent Application Ser. No. 62/036,966, filed Aug. 13, 2014 and U.S. Provisional Patent Application Ser. No. 62/007,694, filed Jun. 4, 2014, which applications are hereby incorporated by reference in their entireties. To the extent appropriate, a claim of priority is made to each of the above disclosed applications.

TECHNICAL FIELD

The present disclosure relates generally to electrochemical sensors and to methods for making.

BACKGROUND

Electrochemical bio-sensors have been developed for sensing (e.g., detecting or measuring) bio-analyte concentrations in fluid samples. For example, U.S. Pat. Nos. 5,264,105; 5,356,786; 5,262,035; 5,320,725; and 6,464,849, which are hereby incorporated by reference in their entireties, disclose electrochemical sensors for sensing analytes, such as lactate or glucose. Electrochemical sensors have been widely used in blood glucose monitoring systems adapted for home use by diabetics to allow blood glucose levels to be closely monitored. Other example types of blood glucose monitoring systems are disclosed by U.S. Pat. Nos. 5,575,403; 6,379,317; and 6,893,545.

SUMMARY

Aspects of the present disclosure relate to electrochemical sensors that can provide a real-time blood analyte reading (e.g., a reading for glucose, lactate or other analyte) while causing the patient minimal discomfort and while not requiring the patient to produce an exposed droplet of blood. In certain examples, the electrochemical sensors have one or more micro features manufactured using advanced printing technology. In certain examples the advanced printing technology includes aerosol jet printing. In certain examples, the electrochemical sensor includes electrodes supported on an electrode carrier such as a micro extrusion positioned within a skin piercing member. In certain examples, electrodes are printed (e.g., aerosol jet printed) on the micro extrusion. In certain examples, sensing chemistry is printed (e.g., aerosol jet printed) on the micro extrusion and/or on the electrodes supported by the micro extrusion. In certain examples, diffusive membranes/coatings, electrically insulating materials or other materials are printed on the micro extrusion and/or the electrodes. In certain examples, the micro extrusion has a ribbon-shaped transverse cross-sectional profile. In certain examples, the ribbon-shaped transverse cross-sectional profile has a flat middle section and enlarged, rounded ends, and wherein electrodes are printed (e.g., aerosol jet printed) on the flat middle section. In certain examples, elongated working, reference and counter electrodes are printed on the flat middle section. In certain examples, the skin piercing member has a diameter equal to or smaller than 28 gauge. In certain examples, the electrochemical sensors are one-time use sensors configured for taking one analyst reading per use. In certain examples, the electro chemical sensors have skin piercing members designed to generate wounds that self-close upon removal of the skin piercing members from the skin. In certain examples, the electro-chemical sensors have analyte analysis zones that extend from a tip of the skin piercing member to a capillary stop defined by the skin piercing member.

In general terms, this disclosure is also directed to a method of manufacturing an analyte sensor using aerosol jet printing. In certain examples, electrodes (e.g., working electrodes, reference electrodes, etc.), electrical contacts, sensing chemistry, electrically insulating layers, diffusive membrane, and/or other structures can be applied to a substrate using the aerosol jet printing techniques. In an example, a glucose sensor is manufactured using aerosol jet printing. In another example, a lactate sensor is manufactured using aerosol jet printing.

In accordance with some aspects of the disclosure, a method for manufacturing a sensor includes printing a working electrode onto a substrate using aerosol jet printing. In certain examples, the method also includes printing sensing chemistry onto the working electrode using aerosol jet printing. In certain examples, the method also includes printing diffusive membrane or coating onto the working electrode over the sensing chemistry using aerosol jet printing. In certain examples, the method also includes printing the substrate using aerosol jet printing.

In certain implementations, printing the sensing chemistry includes printing an enzyme-based ink that includes detection chemistry onto the working electrode, and wherein the sensing chemistry includes an enzyme, a mediator, a buffer, a thickening agent, a binder, and a surfactant.

In certain implementations, printing the working electrode includes printing a pattern having cells and printing sensing chemistry onto the working electrode includes depositing the sensing chemistry within the cells of the pattern. In an example, the pattern includes a honeycomb pattern. In certain examples, the method includes printing a diffusive membrane or coating onto the pattern over the sensing chemistry.

A variety of additional aspects will be set forth within the description that follows. The aspects can relate to individual features and to combinations of features. It is to be understood that both the foregoing general description and the following detailed description are exemplary and explanatory only and are not restrictive of the broad concepts upon which the embodiments disclosed herein are based.

DETAILED DESCRIPTION

Figure 1:
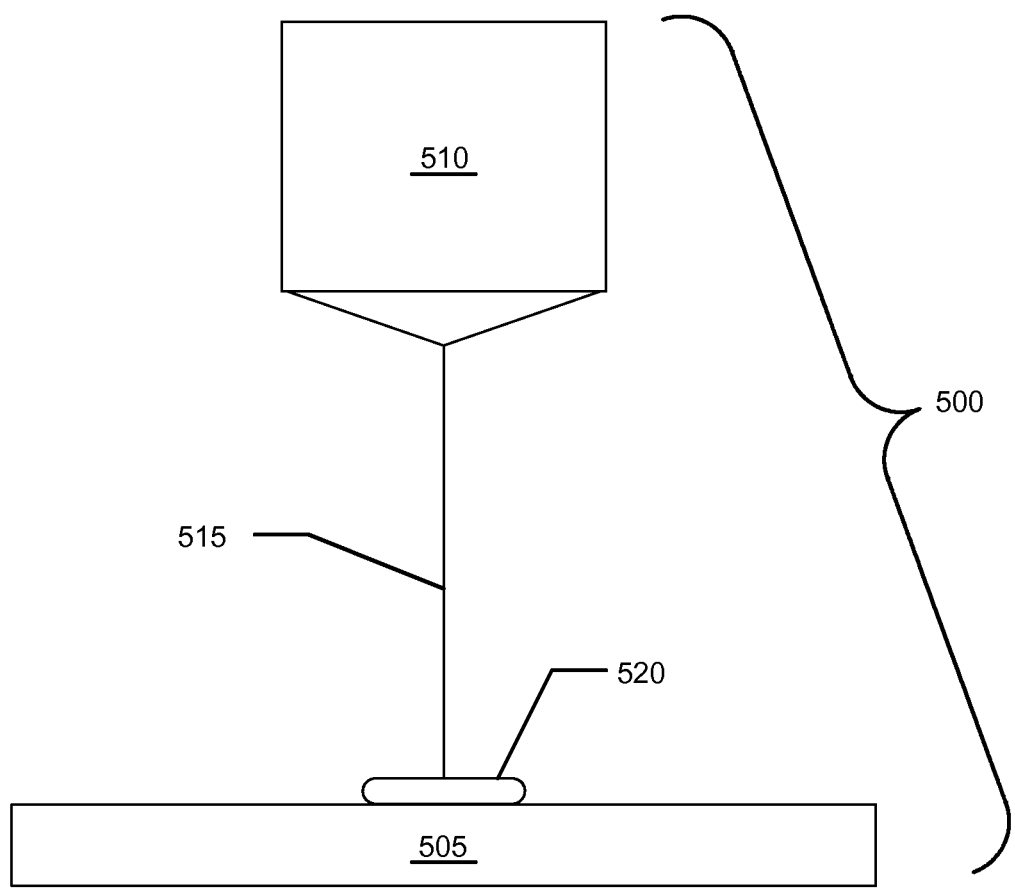
FIG. 1 is schematic view of an example aerosol jet printing system including a printer and a substrate.

Various embodiments will be described in detail with reference to the drawings, wherein like reference numerals represent like parts and assemblies throughout the several views. Reference to various embodiments does not limit the scope of the claims attached hereto. Additionally, any examples set forth in this specification are not intended to be limiting and merely set forth some of the many possible embodiments for the appended claims.

Definitions

The following definitions are provided for terms used herein:

A "working electrode" is an electrode at which the analyte (or a second compound whose level depends on the level of the analyte) is electrooxidized or electroreduced with or without the agency of an electron transfer agent.

A "reference electrode" is an electrode used in measuring the potential of the working electrode. The reference electrode should have a generally constant electrochemical potential as long as no current flows through it. As used herein, the term "reference electrode" includes pseudo-reference electrodes. In the context of the disclosure, the term "reference electrode" can include reference electrodes which also function as counter electrodes (i.e., a counter/reference electrode).

A "counter electrode" refers to an electrode paired with a working electrode to form an electrochemical cell. In use, electrical current passes through the working and counter electrodes. The electrical current passing through the counter electrode is equal in magnitude and opposite in sign to the current passing through the working electrode. In the context of the disclosure, the term "counter electrode" can include counter electrodes which also function as reference electrodes (i.e., a counter/reference electrode).

A "counter/reference electrode" is an electrode that functions as both a counter electrode and a reference electrode.

An "electrochemical sensing system" is a system configured to detect the presence and/or measure the level of an analyte in a sample via electrochemical oxidation and reduction reactions on the sensor. These reactions are converted (e.g., transduced) to an electrical signal that can be correlated to an amount, concentration, or level of an analyte in the sample. Further details about electrochemical sensing systems, working electrodes, counter electrodes and reference electrodes can be found at U.S. Pat. No. 6,560,471, the disclosure of which is hereby incorporated herein by reference in its entirety.

"Electrolysis" is the electrooxidation or electroreduction of a compound either directly at an electrode or via one or more electron transfer agents.

An "electron transfer agent" is a compound that carries electrons between the analyte and the working electrode either directly or in cooperation with other electron transfer agents. One example of an electron transfer agent is a redox mediator.

A "sensing layer" is a component of the sensor which includes constituents that facilitate the electrolysis of the analyte. The sensing layer may include constituents such as an electron transfer agent, a catalyst which catalyzes a reaction of the analyte to produce a response at the electrode, or both.

Aerosol Jet Printing

Aspects of the present disclosure also relate to systems, methods, and techniques for fabricating sensors in accordance with the principles of the present disclosure. In certain examples, electrodes (e.g., working electrodes, reference electrodes, etc.), electrical contacts, sensing chemistry, diffusive membranes, coatings, insulative substrates, and/or other structures can be applied using the aerosol jet printing techniques of the type disclosed in U.S. Pat. No. 8,455,051, which is hereby incorporated by reference herein in its entirety.

In certain examples, the printed electrodes include electrically conductive particles of micrometer and/or nanometer size. The printed electrodes have a geometric surface area that refers to the lateral dimensions of the electrodes. Aerosol jet printing the electrodes provides electrodes with an electrically conductive surface area that is greater than the geometric surface area of the electrodes. Accordingly, the printed electrodes may have a greater ionically accessible surface area compared to other types of electrodes with similar geometric surface area.

As shown in FIG. 1, an example aerosol jet printing system 500 includes a printer 510 having a deposition flow head 512 that directs an aerosol stream 515 of aerosolized material to a substrate 520. The aerosolized material can be delivered to a deposition flow head 512 using a carrier gas. The deposition flow head 512 can direct the aerosolized fluid (i.e., the aerosol stream) toward an orifice. A sheath gas can be directed about the aerosol stream so that the aerosol stream and the sheath gas pass through the orifice. In some implementations, the aerosol stream 515 includes aerosolized or atomized metals (e.g., gold, silver, and platinum), metal oxides, silver/silver chloride, and/or carbon. In other implementations, the aerosol stream 515 includes aerosolized or atomized solution of a liquid molecular precursor or suspension of particles or other materials.

In certain examples, the substrate is a dielectric. In certain examples, the substrate can include a dielectric material such as polyetheretherketone (PEEK), polyimide (e.g., KAPTON®), or other plastic materials. Materials such as glass, metal oxides, silicon wafers, or other materials also can serve as substrates. In certain examples, printing can be applied on conductive substrates, such as carbons and metals. In certain examples, the substrate is elongated and has a profile shape defined by an extrusion process. In certain examples, the aerosol jet printing technique can be used to print on various profiles such as flat strips, ribbons, or various plastic extrusions.

In certain examples, the aerosol jet printing process can allow for the deposition of features with dimensions as small as 10 microns. In certain examples, the aerosol jet printing process can allow for the deposition of features with dimensions as small as 5 microns. In certain examples, the aerosol jet printing process can allow for the deposition of features with dimensions as small as 1 micron.

The various materials can be printed in the form of micrometer sized particles, nanoparticles, nanotubes, or graphene sheets. It will be appreciated that aerosol jet printing technology can allow for the enhanced resolution of a printed pattern and more reproducible deposition characteristics with respect to materials such as gold and silver particles when compared to conventional ink jet printing, screen printing, or spray deposition methods.

In accordance with some aspects of the disclosure, one or more electrodes can be deposited onto one or more sides of the substrate. In some implementations, a working electrode can be deposited on a substrate using an aerosol jet printing process. For example, an aerosol stream including gold can be applied to a substrate. In other implementations, aerosol jet printing techniques can be used to apply a reference electrode to a substrate. For example, the aerosol jet printing technique can be used to deposit a layer including silver or including silver chloride. In the various examples described herein, it will be understood that a printing technique such as aerosol jet printing is applicable wherever features, structures or components are described as being deposited or printed. In certain examples, aerosol jet printing can be used to consecutively precisely deposit conductive material for a working electrode on a substrate such as a micro extrusion followed by sensing chemistry on the conductive material.

Figure 2:
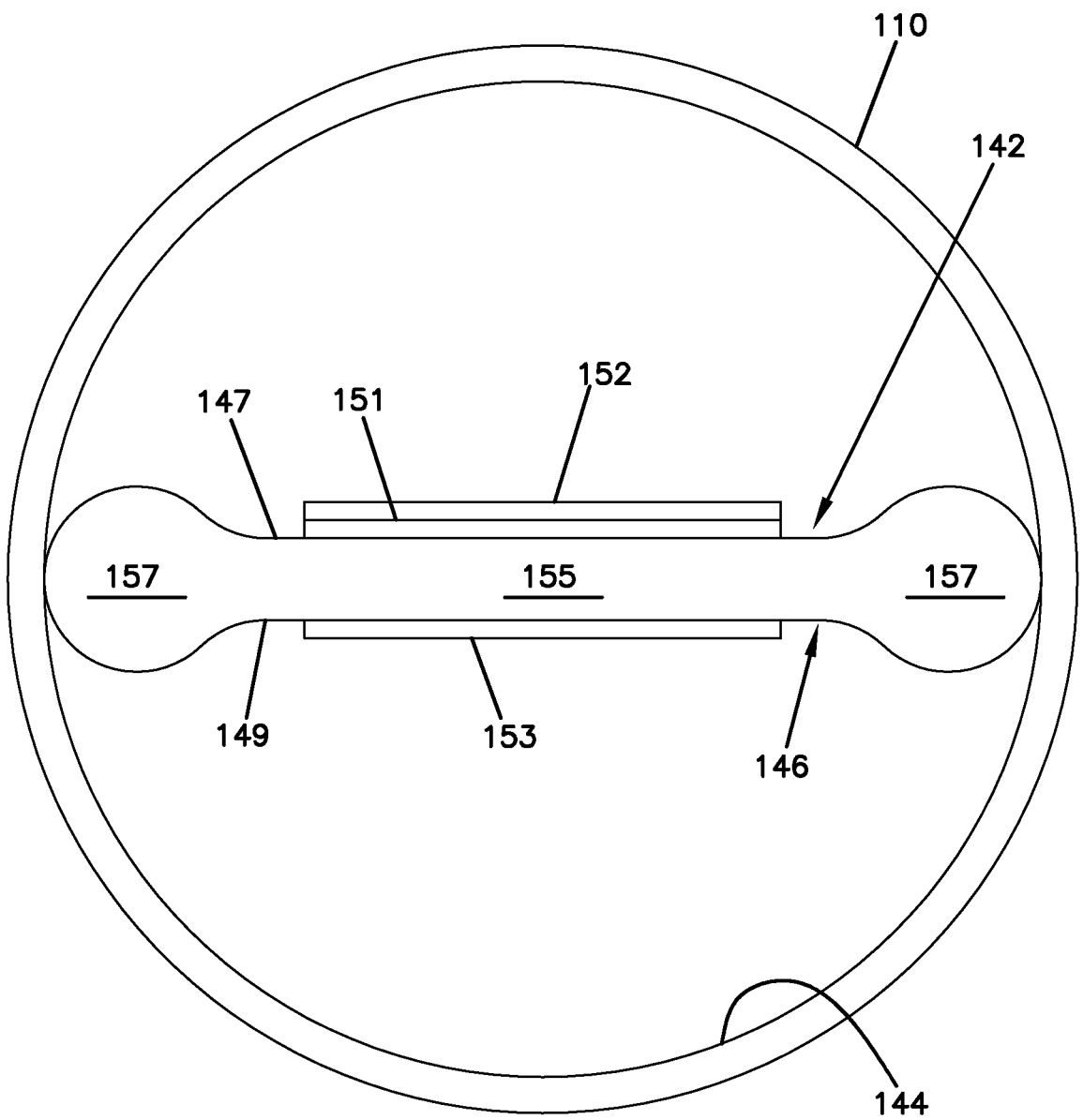
FIG. 2 is a cross-sectional view of a skin piercing member of a sensor module of FIG. 11 containing a working electrode and sensing chemistry printed onto a substrate such as an elongate spacer.

In some implementations, one or more electrodes can be deposited on an elongated dielectric spacer 146 such as the spacer shown at FIG. 2. It will be appreciated that FIG. 2 is a transverse cross-sectional view of the spacer 146 cut through the spacer in an orientation perpendicular to the length of the spacer 146. The electrodes can be deposited as elongated strips or layers that having lengths that run along the length of the elongated spacer 146. In some examples, the spacer 146 is an extruded spacer and can be a micro extrusion. In some examples, the spacer itself can be made through a deposition process such as aerosol jet printing. The elongated dielectric spacer 146 can include opposite first and second sides 147, 149. In one example, the transverse cross-sectional shape of the elongated dielectric spacer 146 has a flat middle section 155 and enlarged, rounded ends 157. In certain examples, a working electrode 151 can be deposited on a first side 147 of the spacer 146. In certain examples, a reference electrode 153 can be deposited on a second side 149 of the spacer 146.

Figure 3:
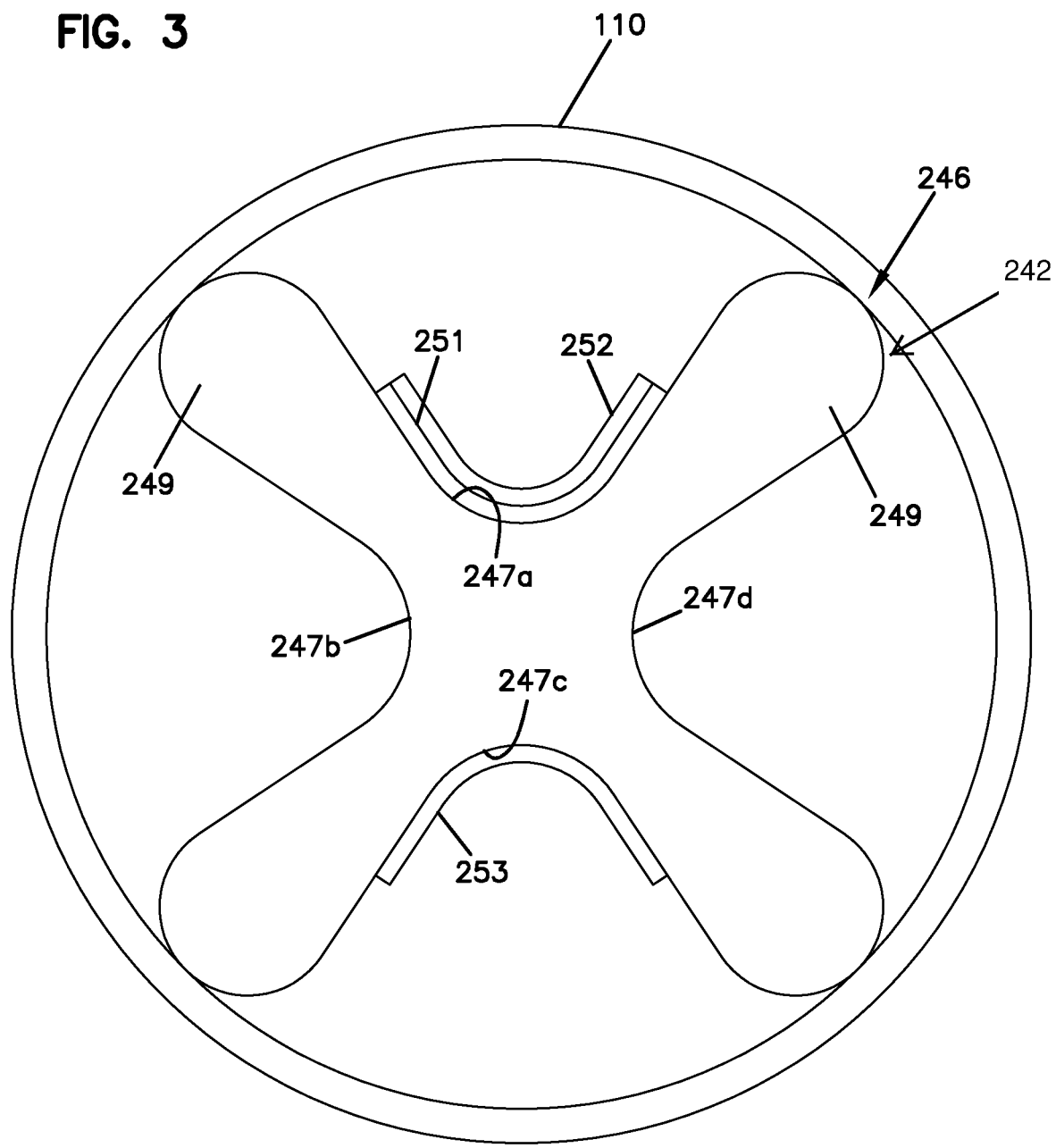
FIG. 3 is a cross-sectional view of the skin piercing member of FIG. 11 containing a working electrode and sensing chemistry printed onto another example substrate such as an elongate spacer having an alternative transverse cross-sectional profile.

In certain implementations, one or more electrodes can be deposited on multi-lobed elongated spacers. For example, one or more electrodes can be deposited on a multi-lobed spacer 246 of the type shown at FIG. 3. It will be appreciated that FIG. 3 is a transverse cross-sectional view of the spacer 246 cut through the spacer in an orientation perpendicular to the length of the spacer 246. The electrodes can be deposited as elongated strips or layers that having lengths that run along the length of the elongated spacer 246. In some examples, the spacer 246 is an extruded spacer and can be a micro extrusion. In some examples, the spacer itself can be made through a deposition process such as aerosol jet printing. In an example, a working electrode 251 can be deposited along a leg 249 of the spacer 246. In an example, the working electrode 251 can be deposited between a first pair of legs 249 of the spacer 246 (see FIG. 3). In an example, a reference electrode 253 can be deposited between a different pair of legs 249 of the spacer 246 (see FIG. 3). In an example, the reference electrode 253 can be deposited along a leg 249 of the spacer 246.

Figure 4:
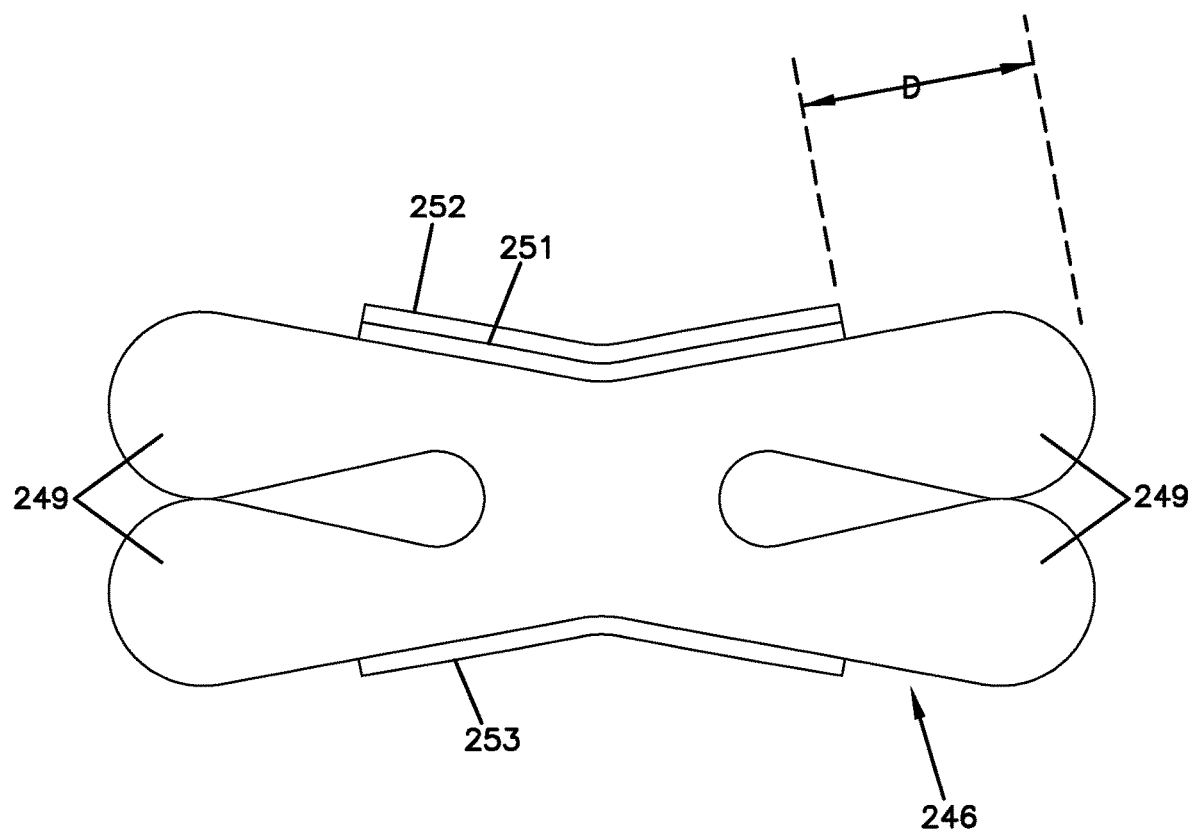
FIG. 4 shows the spacer of FIG. 3 in a compressed orientation.

In some examples, aerosol jet printing of an electrode onto a multi-lobed substrate can be facilitated by deforming the substrate to define a flatter deposition surface or a larger angle between legs of the substrate. For example, FIG. 4 shows the multi-lobed substrate 246 of FIG. 3 with a first pair of legs 249 squeezed together at a left side of the paper and a second pair of legs 249 squeezed together at a right side of the paper. Such a configuration enlarges the angle between the top two legs 249 and enlarges the angle between the bottom two legs 249. The enlarged angle facilitates deposition of an electrode on the surface between the top two legs 249 and/or on the surface between the bottom two legs 249.

Figure 5:
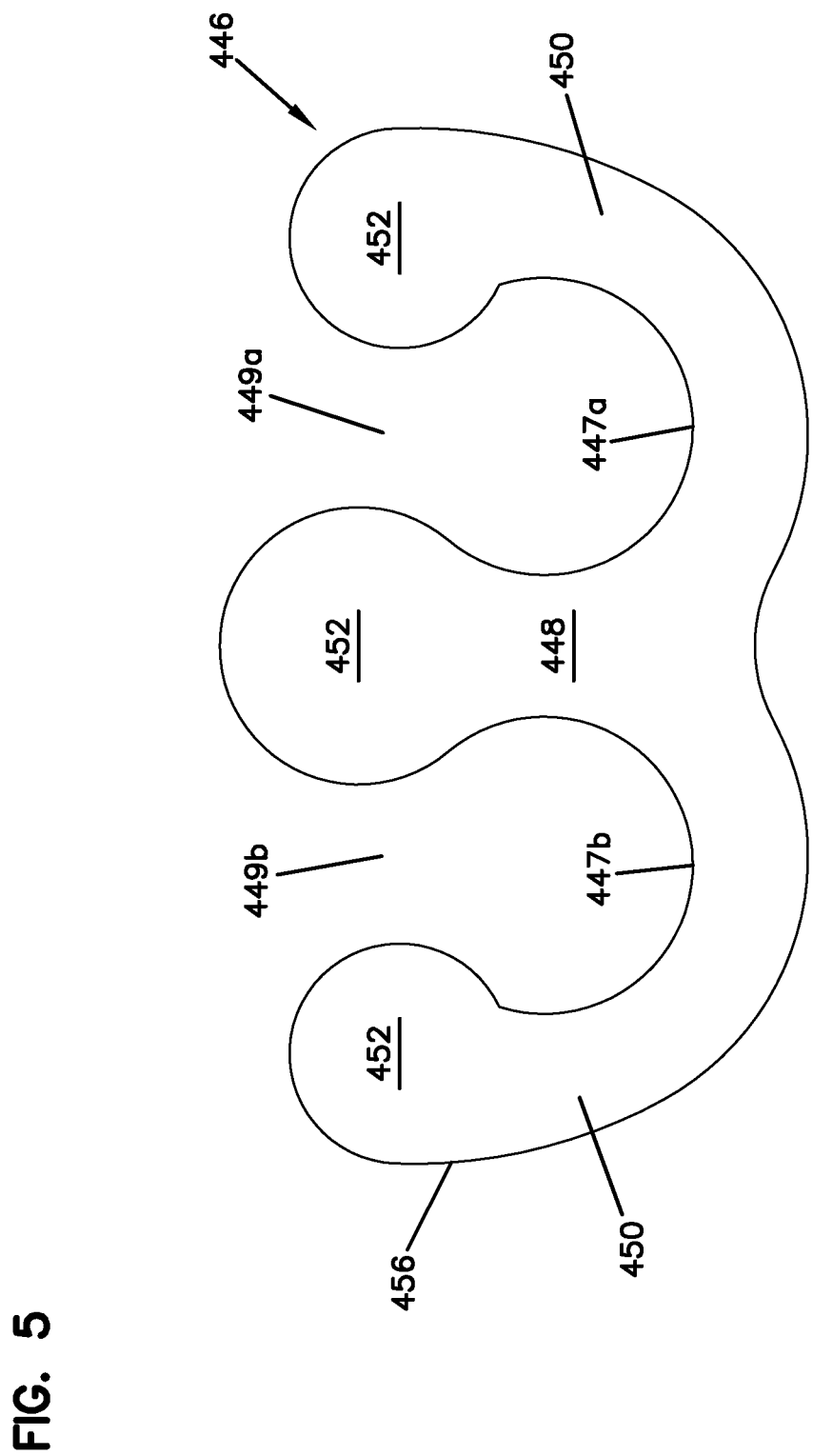
FIG. 5 is a cross-sectional view of the skin piercing member of FIG. 11 containing a working electrode and sensing chemistry printed onto another example substrate such as an elongate spacer having an alternative transverse cross-sectional profile.

In certain implementations, one or more electrodes can be deposited in on elongated spacers. For example, one or more electrodes can be deposited in pockets 447a, 447b of a spacer 446 of the type shown at FIG. 5. FIG. 5 is a transverse cross-sectional view of the spacer 446. In an example, a working electrode can be deposited in the first pocket 447a of the spacer 446. In an example, a reference electrode can be deposited in a second pocket 447b of the spacer 446. In an example, an electrode can be deposited on a different portion of the spacer 446.

Figure 6:
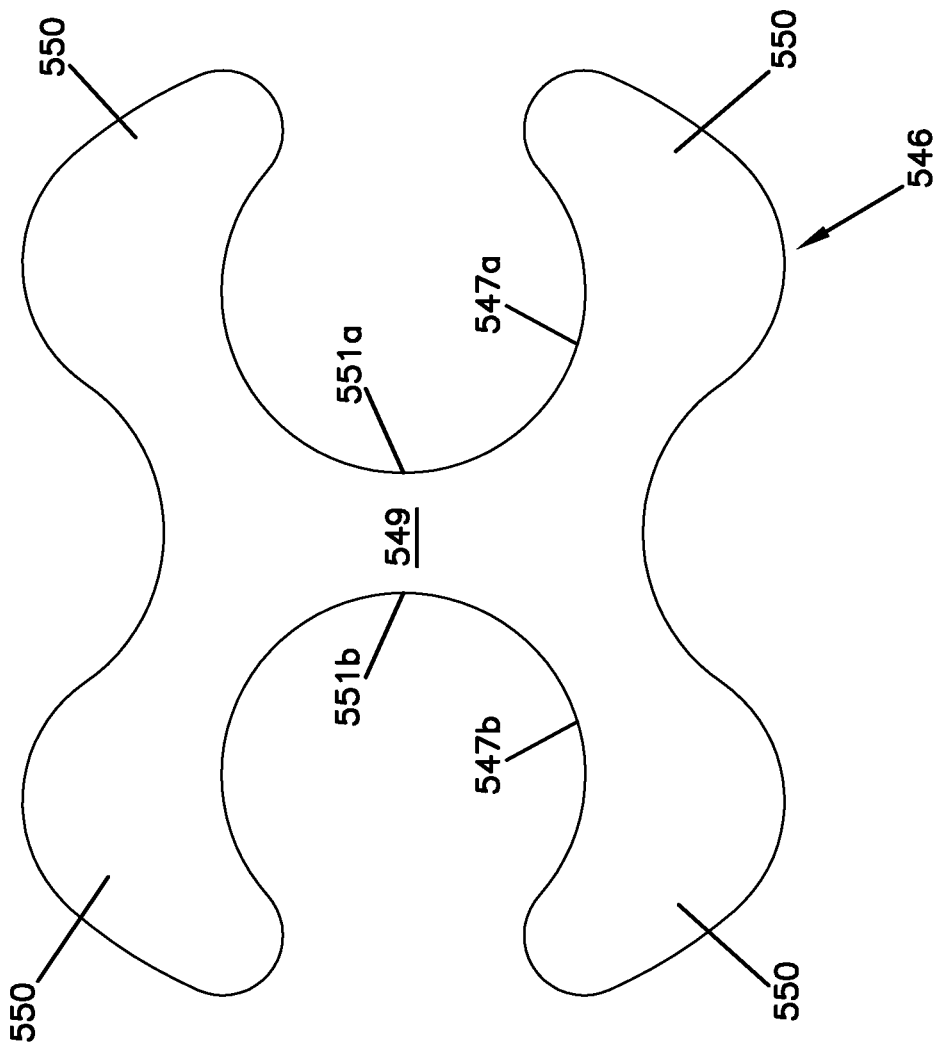
FIG. 6 is a cross-sectional view of the skin piercing member of FIG. 11 containing a working electrode and sensing chemistry printed onto another example substrate such as an elongate spacer having an alternative transverse cross-sectional profile.

In other examples, one or more electrodes can be deposited in pockets 547a, 547b of an elongated spacer 546 of the type shown at FIG. 6. In an example, a working electrode can be deposited in the first pocket 547a of the spacer 546. In an example, a reference electrode can be deposited in a second pocket 547b of the spacer 546. In an example, an electrode can be deposited on a different portion of the spacer 546.

Figure 7:
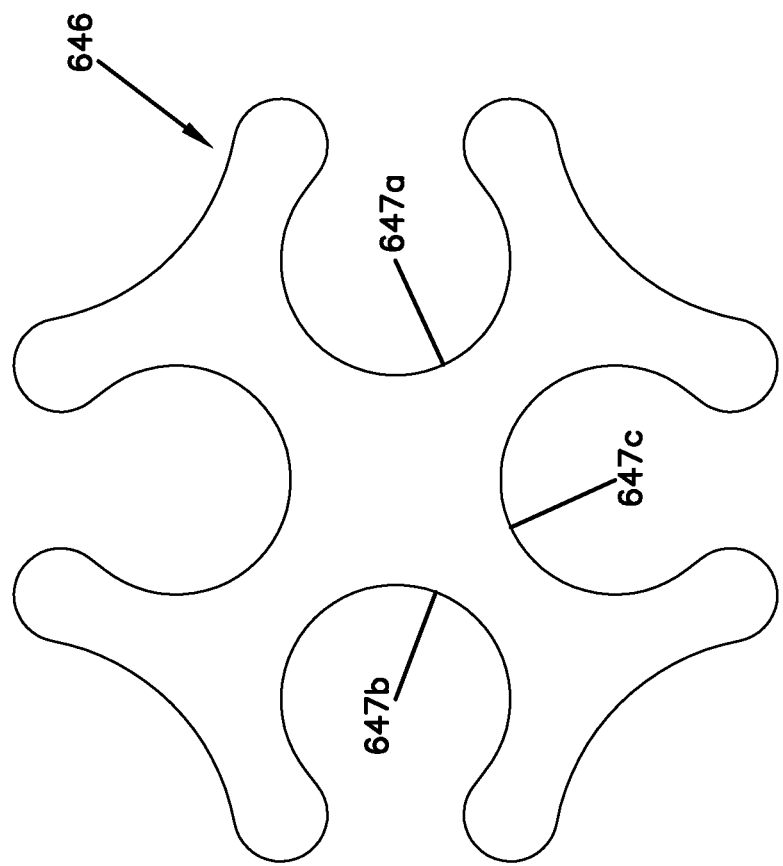
FIG. 7 is a cross-sectional view of the skin piercing member of FIG. 11 containing a working electrode and sensing chemistry printed onto another example substrate such as an elongate spacer having an alternative transverse cross-sectional profile.

In other examples, one or more electrodes can be deposited in pockets 647a, 647b of an elongated spacer 646 of the type shown at FIG. 7. In an example, a working electrode can be deposited in the first pocket 647a of the spacer 646. In an example, a reference electrode can be deposited in a second pocket 647b of the spacer 646. In an example, an electrode can be deposited on a different portion of the spacer 646.

In each of the examples of FIGS. 2-7, the spacers 146, 246, 346, 446, 556 and 646 are shown within the lumen of an elongated skin piercing member 110. The spacers extend through the length of the skin piercing member and the electrodes run along a length of the skin piercing member and the spacers.

Aerosol jet printing also allows for the more flexible sizing of working electrodes and reference electrodes. For example, the relative sizes of the working electrode and the reference electrode can be precisely controlled. In certain examples, the working electrode can be larger than the reference electrode. It will be appreciated that aerosol jet printing techniques also have various technical advantages when compared to more conventional techniques relating to the speed of application, the ability to precisely print small shapes, and ease of automation.

In certain examples, the aerosol jet printing system 500 can produce electrodes having larger active surface area or unit boundary area as compared to traditional coating techniques such as sputtered metal coating, evaporated metal coating, chemical vapor deposition techniques, or other coating techniques. For example, aerosol jet printing techniques can produce sintered metal nanoparticle having a texture that results in the larger active surface area or unit boundary area compared to other coating techniques. Such enhanced active surface area increases the measured current of the sensor. The current increase can be advantageous for enhancing the precision of blood glucose measurement.

In certain examples, aerosol jet printing system 500 can produce thicker electrodes as compared to electrodes formed by conventional coating techniques, such as sputtered metal coating techniques, evaporated metal coating techniques, and chemical vapor deposition coating techniques. This allows for higher electrical conductivity of the produced electrodes and, in turn, more precise measurement of glucose concentration.

In accordance with certain aspects of the disclosure, aerosol jet printing can be applicable for the application of enzyme-based ink that contains detection chemistry (e.g., glucose detection chemistry, lactate detection chemistry, etc.). For example, the enzymatic ink can be aerosol jet printed over or adjacent a working electrode on a substrate. In an example, the ink is a conductive ink (e.g., a carbon based ink). In certain examples, aerosol jet printing can be used to apply carbon-based conductive ink used in electrode formation. In certain examples, aerosol jet printing can be applicable for a wide range of ink viscosities ranging from 0.7 to 2500 centipoise.

In certain examples, aerosol jet printing can be used to deposit enzymatic ink with controlled mass loading and/or spatial distribution. For example, in certain examples, aerosol jet printing can be used to deposit glucose detection chemistry with precise control over its mass loading and spatial distribution as compared to other application techniques such as dipping methods.

In certain examples, the detection chemistry applied by the aerosol jet printing technique can have a composition including a plurality of component parts such as: (a) an enzyme that catalyzes the oxidation of an analyte (e.g., glucose) in a blood sample; (b) a mediator that facilitates the transfer of electrons and protons generated in enzyme catalyzed analyte oxidation to the working electrode's electrically conductive surface; (c) a buffer used to stabilize the applied enzyme; (d) a surfactant; (e) a binder; and (f) a thickening agent. Example enzymes used to sense glucose include glucose oxidase and glucose dehydrogenase.

It will be appreciated that mediators facilitate the transfer of electrons and protons generated in enzyme catalyzed glucose oxidation to the working electrode electrically conductive surface where the mediator is electrochemically oxidized. An immobilized and diffusive mediator can be used. Example mediators include potassium ferricyanide or benzoquinone (BQ).

It will be appreciated that a buffer is used to stabilize applied enzymes used during the synthesis, deposition, curing, and storage of the sensing chemistry. The buffer functions to adjust the pH of a blood sample to enhance and unify enzyme kinetics. In certain examples, the buffer has a relatively low ionic strength so as to avoid coagulation of the enzyme. Example buffers include potassium phosphate or HEPES (4-(2-hydroxyethyl)-1-piperazineethanesulfonic acid).

It will be appreciated that binders are used to mechanically attach enzyme, mediators, buffers, and all other sensing chemistry to the sensor in a dry state after chemistry deposition and curing. It will be appreciated that it is beneficial if the binder chemically binds to the applied surface. The binder facilitates loading of the various sensor components to the substrate of the sensor upon chemistry deposition. In certain examples, the binder is inactive in the enzymatic and charged transfer reaction. In certain examples, the binder does not affect enzyme stability. Non-limiting examples of suitable binders include polyethylene glycol (PEG), polyvinyl alcohol (PVA) or a PVA-PEG copolymer.

It will be appreciated that thickening agents are used to increase the viscosity of the chemistry in order to support and facilitate chemistry loading and immobilization on the applied surface. In certain examples, the thickening agent should not affect enzyme stability, activity, or the pH of the blood sample. Example thickening agents includes polyvinyl alcohol (PVA), polyurethane, and latex.

In accordance with some aspects of the disclosure, the electrically conductive electrodes can be printed on a substrate using aerosol jet printing to form 3D patterns. For example, in certain implementations, the electrically conductive electrodes can be printed to form 3D patterns of increased geometric surface area. The patterns may form, for example, honeycombs, circular, square, or rectangular cells. Sensing chemistry can be subsequently deposited within the cells. This configuration may support mechanical stability and retention of the sensing chemistry in the working electrode.

In some implementations, a diffusive membrane or coating may be printed over the top of the sensing chemistry and 3D conductive pattern. In certain implementations, printing the diffusive membrane or coating over the sensing chemistry enhances a linear detection regime of the sensor. For example, the diffusive membrane or coating may reduce the amount of analyte reaching the sensing chemistry during the testing period, thereby inhibiting saturation of the sensing chemistry. Extending a length of time before saturation may enhance the accuracy of the sensor readings and/or reduce sensor errors. In certain implementations, printing the diffusive membrane or coating over the sensing chemistry encapsulates the sensing chemistry on the working electrode. This encapsulation inhibits leaching of the sensing chemistry or the printing ink (e.g., the mediator) from the sensor. Inhibiting such leaching reduces the likelihood that such components will be transferred into the body of the user. In certain implementations, printing the diffusive membrane or coating over the sensing chemistry enhances the shelf life of the sensor by maintaining protective microenvironment for the enzymes in the deposited sensing chemistry.

Figure 8:
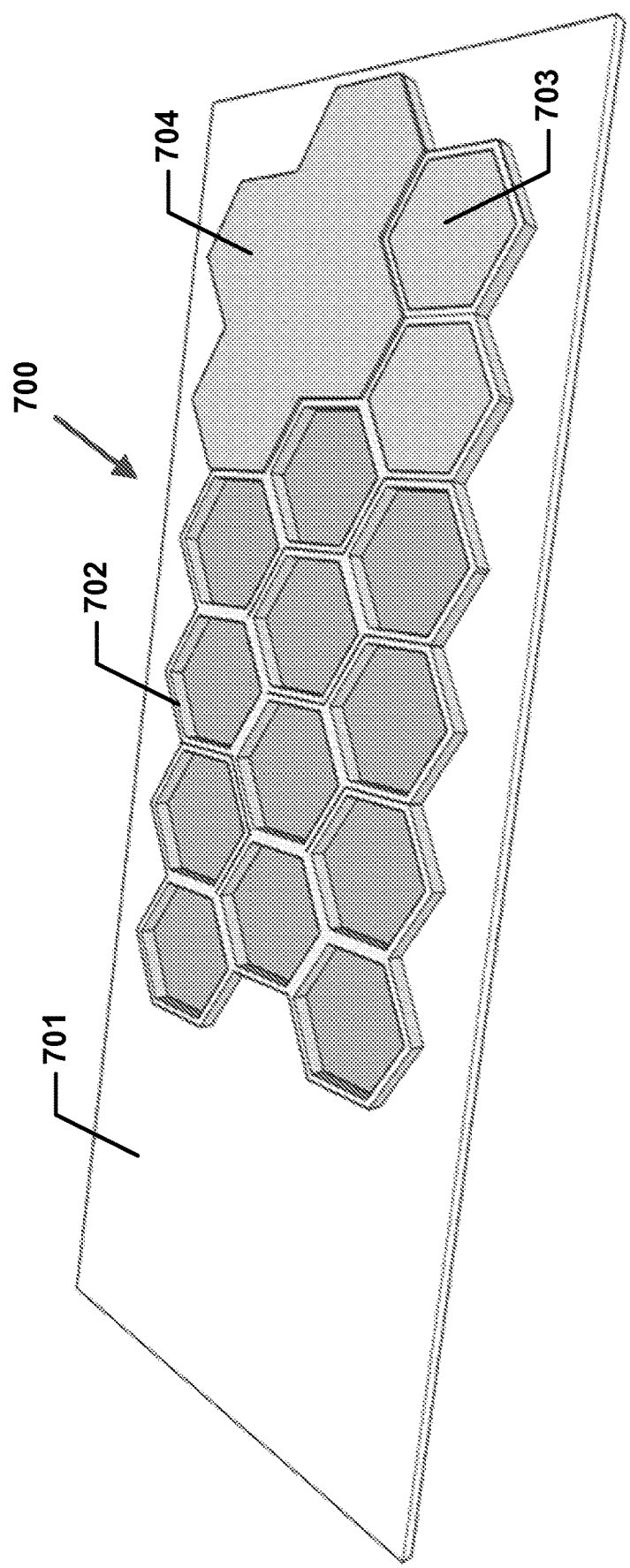
FIG. 8 illustrates an example 3D pattern printed on an electrically insulating substrate.

For example, FIG. 8 illustrates an example 3D pattern 700 printed on an electrically insulating substrate 701. The pattern 700 includes conductive electrodes 702. In the example shown, the conductive electrodes 702 form a 3D honeycomb pattern. In certain implementations, the pattern 700 also can include sensing chemistry 703 printed over the conductive electrodes 702. In the example shown, the sensing chemistry 703 can be printed within cells of the honeycomb pattern 702. In certain implementations, the pattern 700 also includes a diffusive membrane or coating 704 disposed over the electrodes 702. In the example shown, the diffusive membrane or coating 704 can be printed over the cells of the honeycomb pattern 702 to cover the sensing chemistry 703. In other examples, the conductive electrodes 702 can be printed in any desired shape. In certain examples, the spacer 701 can be printed using aerosol jet printing.

Figure 9:
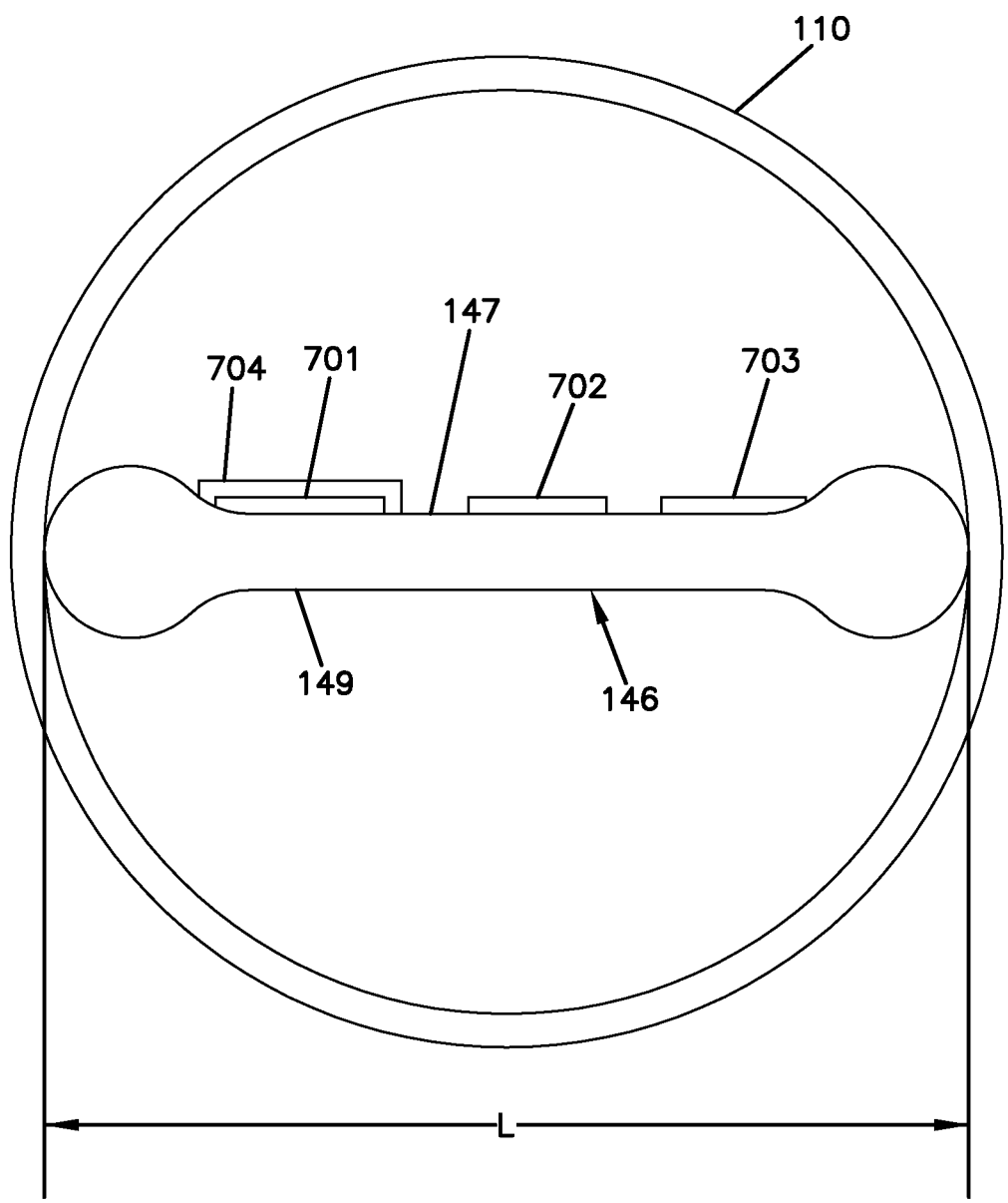
FIG. 9 illustrates another electrode configuration printed on the elongate spacer of the FIG. 2.

FIG. 9 shows a 3-electrode electrochemical sensing system in accordance with the principles of the present disclosure. The sensing system includes the spacer 146 of FIG. 2 which is positioned within the lumen of the skin piercing member 110. In one example, the spacer 146 is a micro extrusion having a transverse cross-sectional profile define a length a length L less than or equal to 0.007, 0.006 or 0.005 inches. In one example, the length L is measured from one rounded end 157 to the other rounded end 157 of the transverse cross-sectional profile of the spacer. In one example, two or more electrodes are printed on one side of the transverse cross-sectional profile of the spacer 146. In one example, working, counter and reference electrodes 701, 702, 703 are printed at one side of the spacer 146 (e.g., on side 147). In one example, sensing chemistry 704 is printed on one side of the spacer 146 (e.g., on side 147). In one example, the sensing chemistry is printed on the working electrode and/or can be printed elsewhere on the side 147 spacer 146. In some examples, the sensing chemistry can be printed or otherwise provided on the reference and/or counter electrodes or can be provided on portions of the spacer 146 that do not coincide with an electrode.

Sensor Module

Figure 10:
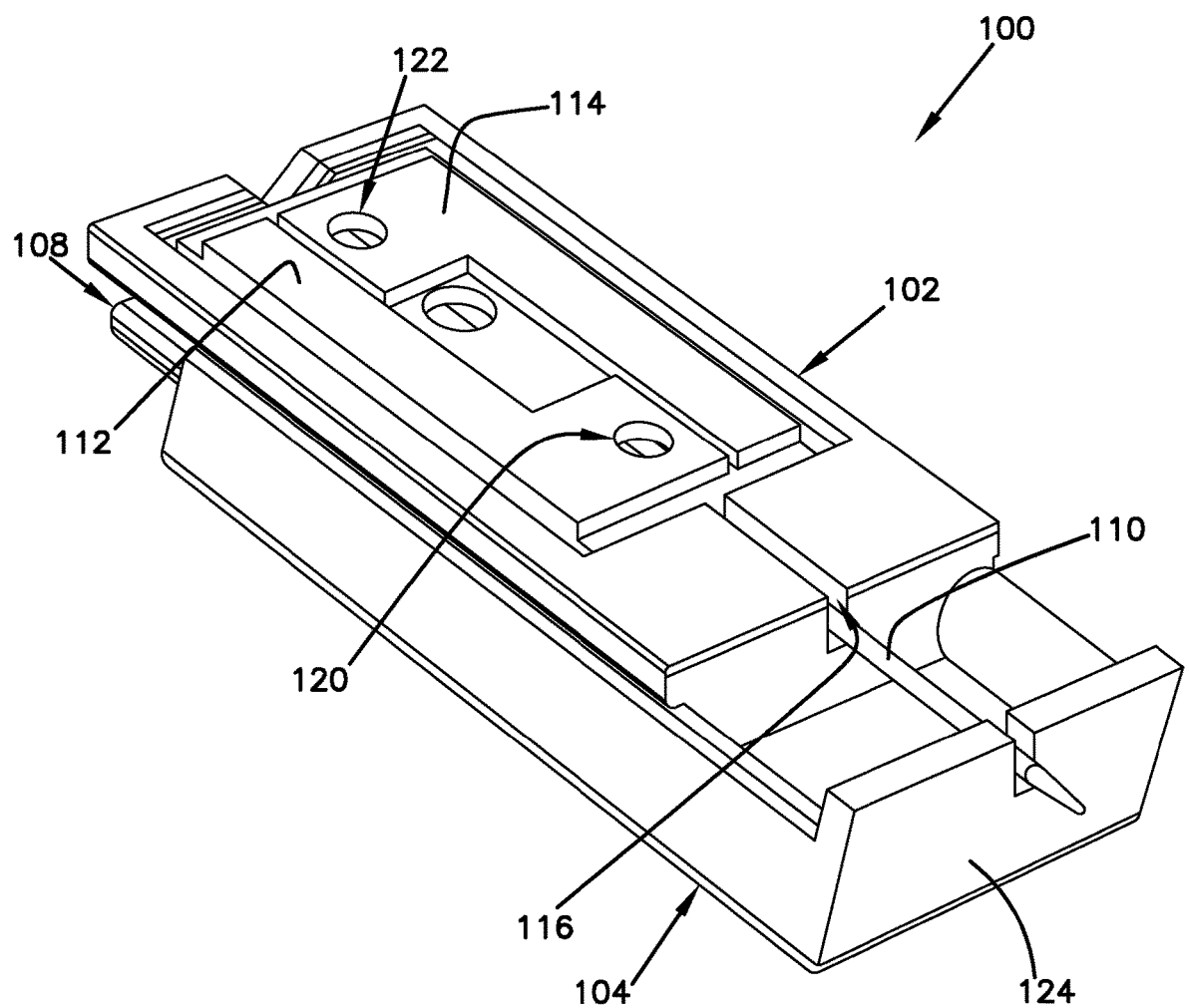
FIG. 10 is perspective view of a sensor module in accordance with the principles of the present disclosure.
Figure 11:
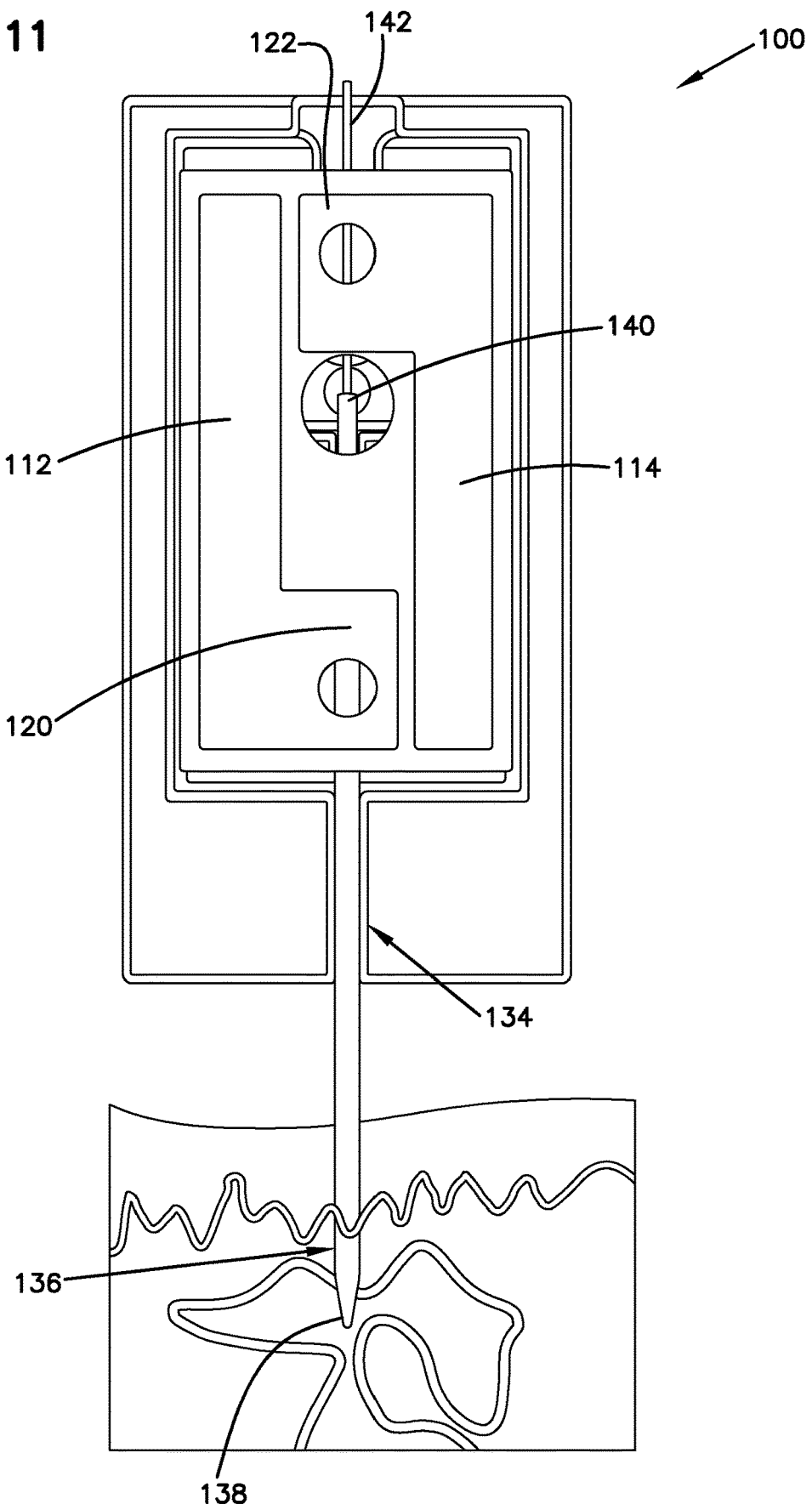
FIG. 11 is a top view of the sensor module of FIG. 1 with a skin piercing member of the sensor module in an extended position inserted in a vascular plexus.
Figure 12:
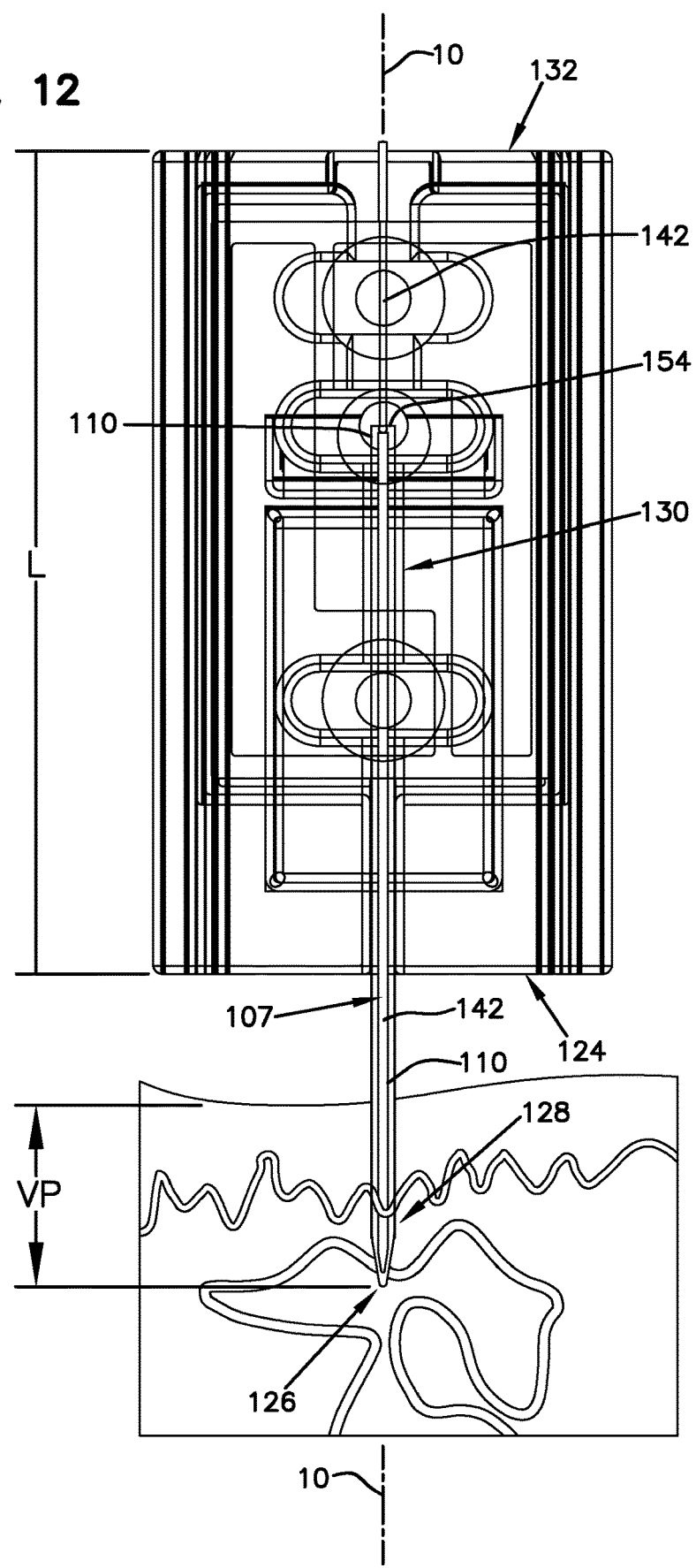
FIG. 12 is a plan view of the sensor module of FIG. 2 with various cross-section lines depicted.

The above printing techniques for electrodes, detection chemistry, and other components can be applied to manufacture sensor modules (e.g., for glucose, lactate, or another analyte). In general, an example of a sensor module 100 (see FIGS. 10-12) includes a carrier 102, a skin piercing member 110 (e.g., a needle), a base 104, and two electrical contacts 112, 114. In certain examples, the skin piercing member 110 is hollow and defines an interior lumen that forms a blood analysis cell. In some implementations, a working electrode is positioned within the lumen and the skin piercing member 110 functions as a counter electrode.

In one example, the skin piercing member 110 is manufactured of an electrically conductive material (e.g., stainless steel) and itself functions as a counter electrode without the need of electrically conductive coatings. In certain examples, the sensor module 100 is a 3-electrode sensor having separate working, reference and counter electrodes. In certain examples, the skin piercing member is a needle in the range of 28-31 gauge. In other examples, the skin piercing member has a diameter that is less than or equal to the diameter of a 26 gauge wire. In certain examples, a blood analysis test cell is provided in the skin piercing member. In certain examples, during testing, a portion of the carrier 102 is subcutaneous and a portion extends outside the body. In certain examples, the blood analysis test cell fills passively with blood during testing.

The carrier 102 is arranged and configured to slideably move along the base 104 between positive stops. In one example, the piercing member 110 is fixed relative to the carrier 102 such that the piercing member 110 is carried by the carrier 102 as the carrier 102 slides relative to the base 104. The skin piercing member 110 is movable with the carrier 102 between a retracted position and an extended position relative to the base 104.

The electrical contacts 112, 114 mount on the carrier 102. The contacts 112, 114, respectively, have contact tabs 120, 122. Tab 120 can be used to electrically connect the contact 112 to the skin piercing member 110 which can be adapted to function as a counter electrode. Tab 122 can be used to electrically connect the contact 114 to a working electrode having a portion that extends into the skin piercing member 110 and a portion that extends axially outwardly from a base end of the piercing member 110. An additional tab can be provided to electrically connect to a reference electrode having a portion that extends into the skin piercing member 110 and a portion that extends axially outwardly from a base end of the skin piercing member 110.

The contacts 112, 114 can include structures for electrically connecting the sensor module 100 to a sensor control system. In one example, in use, the sensor control system applies a voltage across the working and counter electrodes and through a blood sample contained within a lumen of the skin piercing member 110. The skin piercing member 110 can have an electrically conductive construction that is exposed to the blood sample during testing so that it can function as the counter electrode. A voltage can be applied through the blood sample between the working electrode and the counter electrode to drive a desired electrochemical reaction in the blood sample within the skin piercing member 110.

In one example, the skin piercing member 110 is hollow and defines an interior lumen in which a working electrode is positioned. The interior lumen can form a blood analysis cell. In certain examples, the skin piercing member 110 is relatively small so as to reduce pain associated with skin piercing and to minimize or prevent extra blood from being exposed at the puncture site. In certain examples, the skin piercing member 110 is 31-28 gauge or smaller in diameter. The working electrode can be formed by a conductive layer (e.g., a gold layer) positioned within the interior lumen of the skin piercing member 110.

A sensing chemistry can be provided within the lumen. In certain examples the sensing chemistry can cover the conductive layer of the working electrode. In other examples the sensing chemistry can be separate from the conductive layer of the working electrode. In certain examples, the sensing chemistry can have a dry, dielectric property/characteristic prior to being exposed to the blood sample, and can be configured to rapidly dissolve and become conductive when exposed to the blood sample. Thus, it is not necessary for the sensing chemistry to be present on the working electrode prior to testing, as long as the blood sample solution including the dissolved sensing chemistry is in contact with the working electrode during testing. Since the sensing chemistry dissolves during testing, it can be provided at various locations within the skin piercing member that will be exposed to blood (e.g., on the inner wall of the skin piercing member, on the working electrode, on the counter electrode, on a dielectric spacer supporting the working and counter electrodes or elsewhere). In use, the thickness of sensing chemistry is preferably selected such that the entire thickness rapidly dissolves and/or is wetted so as to become electrically conductive. The interior volume of the skin piercing member 110 can function as a test zone when filled with a blood sample. The sample analysis zone can provide for specific control of interrelated parameters such as active electrode area, response time, sensitivity, and drift to be engineered in as byproducts of static component features.

Figure 14:
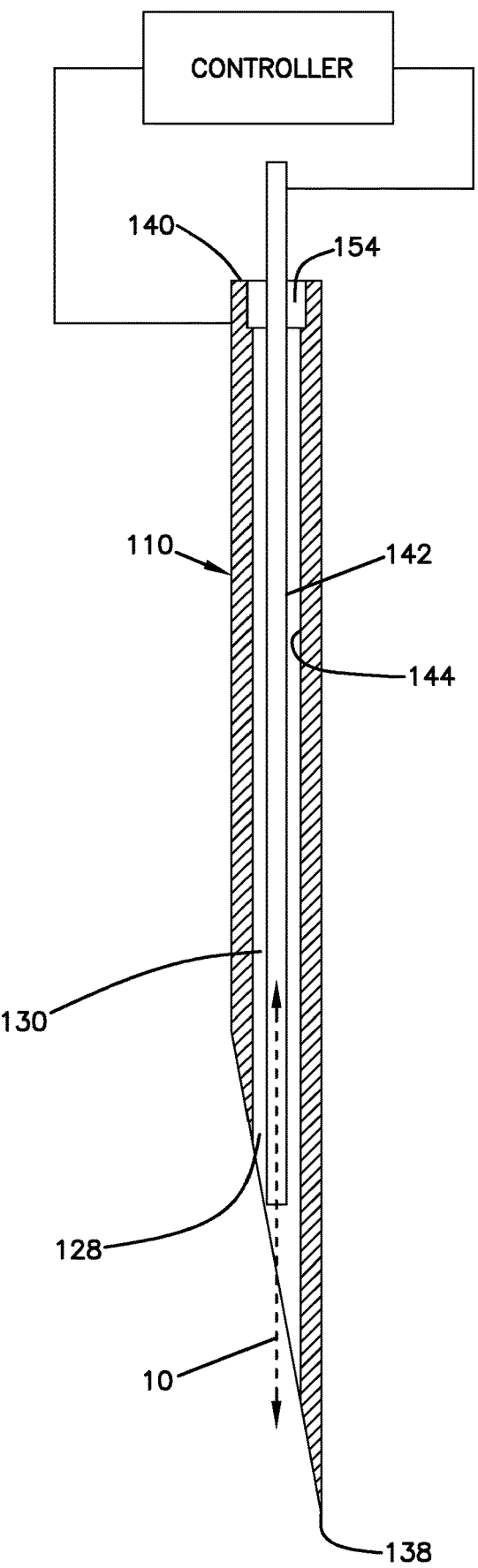
FIG. 14 is a schematic view of the sensor module of FIG. 10.

FIG. 14 is a schematic view showing the skin piercing member 110 having the base end 140 and a tip end 138 (e.g., an insertion end). The skin piercing member 110 defines a lumen 144 that extends through the entire length of the skin piercing member 110 along an axis 10 (e.g., a skin piercing member axis or a lumen axis). A capillary stop 154 can be provide adjacent the base end 140. An elongated sensing component 142 is positioned within the lumen 144 and can have a lower end within 0.5 millimeters of the tip 138 and an upper end portion that extends out of the lumen 144. The elongated sensing component 142 can includes an elongated working electrode and an elongated reference electrode supported by an elongated dielectric spacer. A sensing chemistry can be provided within the lumen 144. In one example, the reference electrode, the working electrode and the sensing chemistry can be aerosol jet printed on the dielectric spacer. In one example, the sensing chemistry can include an enzyme and a mediator for facilitating sensing an analyte, such as glucose. The lumen 144 defines an analysis zone 130 within which blood can flow and the electrochemical reactions (e.g., between the sensing chemistry and the analyte) can take place. The analysis zone 130 can be defined by the interior volume of the skin piercing member 110 less the volume of the elongated sensing component 142. The skin piercing member 110 can have an electrically conductive construction (e.g., stainless steel). The skin piercing member 110 can function as a counter electrode when a blood sample is provided within the analysis zone 130. The blood sample can provide an electrical connection between the counter electrode and the working electrode. A control unit can interface with the working electrode, the counter electrode, and the reference electrode.

In use, the skin piercing member is inserted into the skin to a depth less than 3 millimeters such that the tip 138 resides in the capillary bed. As so positioned, first portions of the working and reference electrodes are subcutaneous and second portions of the working and reference electrodes extend outside the body beyond the skin. Upon insertion, the combination of vascular pressure and capillary action causes a blood sample to rapidly fill the lumen 144 and to contact the working and reference electrodes within the skin piercing member 110. The blood sample also contacts a conductive portion of the skin piercing member 110. The blood flows up the lumen to the capillary stop 154. The volume of space defined within the skin piercing member from the tip 138 to the capillary stop 154 forms an analysis zone 130 having a length that corresponds to a length of the working electrode. The capillary stop 154 ensures that the surface area of the working electrode that is exposed to the blood sample is precisely controlled (i.e., the active surface area of the working electrode corresponds to the length of the working electrode that extends below the capillary stop 154 and is exposed to the blood sample). Applying a voltage between counter and working electrodes causes the oxidation/reduction of glucose in the analysis zone, thereby generating a current at the working electrode that can be measured to sense a concentration of glucose in the blood sample. Control circuitry can apply the voltage, measure the current, and provide a display showing a reading indicating the glucose level. The reference electrode assists in stabilizing the potential applied between the working and counter electrodes.

The sensor module 100 is relatively compact and disposable. For example, in one implementation, the sensor module 100 is generally rectangular in shape and has a length that is less than 1 inch. The sensor module 100 includes opposite major sides and opposite minor sides that extend along the length of the sensor module 100.

The skin piercing member 110 of the sensor module 100 includes a skin piercing end 136 having a sharp tip 138 and a base end 140. The tip 138 of the skin piercing member 100 penetrates the skin of a patient and can be configured to provide a cutting action that generates a wound that self-closes upon removal of the piercing member 110 from the skin. The skin piercing member 110 can be a cannula, needle, or other similar structure preferably having a hollow interior. In this example, the sensor is configured to allow the analysis of the fluid sample to take place entirely within the skin piercing member 110. The skin piercing member 110 provides a volume or reservoir (e.g., the inner lumen) for collecting blood received from a skin puncture site caused by the skin piercing member 110.

In one example, the skin piercing member 110 has an electrically conductive construction suitable for allowing the skin piercing member 110 to function as a counter electrode that works in association with the working electrode contained within the lumen of the skin piercing member 110. In one example, the skin piercing member 110 has a bare metal construction. In one example, the skin piercing member includes stainless steel. The skin piercing member 110 can be about 28-31 gauge or smaller in diameter to allow for an insertion into a patient's skin tissue without creating either a blood producing wound or noticeable pain or discomfort upon insertion. The skin piercing member 110 can have a length of about 12 to 13 mm. In one example, only a relatively short length of the piercing member 100 extends beyond the base 102 when the carrier is slid to an extended position. In one example, the module 100 is configured such that the insertion depth of the skin piercing member 110 will not exceed 2 millimeters. In another example, the skin insertion depth of the skin piercing member 110 is in the range of about 1.5 to 2 mm. This depth of piercing allows for the sensor in the sensor module 100 to communicate with the vascular plexus (VP) dermal layer of tissue. At this depth, the sensor encounters capillary blood that is representative of cellular glucose.

In use of the sensor module 100, a contact end 124 of the base 104 is placed against a patient's skin at a sampling site where it is desired to take a fluid (e.g., blood) sample. Once the contact end 124 is in contact with the skin, the skin piercing member 110 is moved from the retracted position to the extended position (e.g., by sliding the carrier 102 relative to the base 104), thereby causing the tip 138 of the skin piercing member 110 to pierce the patient's skin. Upon insertion of the skin piercing member 110, blood from the capillary field fills the skin piercing member 110. Blood flow is caused at least in part by vascular pressure within the capillary bed.

Capillary action also moves blood upwardly within the piercing member 110 to fill a sample analysis zone 130 within the piercing member 110. At the sample analysis zone 130, an analyte level (e.g., blood glucose level) in the blood sample is sensed through the use of a three-electrode sensor arrangement including an elongated working electrode (WE) (FIG. 4) and an elongated reference electrode (RE) positioned inside the piercing member 110, and a counter electrode formed by the skin piercing member 110. In certain examples, the working and reference electrodes can be conductive fibers, wires, or other elongated members supported by a dielectric spacer. In other examples, the working and reference electrodes can include elongated conductive layers applied to an elongated dielectric spacer. In certain examples, the working and reference electrodes as well as sensing chemistry can be applied on to the elongated dielectric spacer by a printing process such as aerosol jet printing. The elongated conductive layers can have lengths that extend along a corresponding length of the dielectric spacer. In other examples, working, reference and counter electrodes can be printed on the elongated electrode.

In some examples, a test is initiated by pressing an actuator button (not shown) on top of a meter (not shown) while holding the sensor module 100 on the test site (i.e., forearm or fingertip). This action causes a sequence of motions moving the sensor module 100 from a position within the sensor module 100 to an opening in the bottom of the meter. The meter can be placed on the approved testing site, (i.e., forearm or finger). The actuator button can be pressed again following a prompt causing the carrier 102 of the sensor module 100 carrying the skin piercing member 110 to move rapidly forward inserting the skin piercing member 110 to a prescribed depth. The skin piercing member 110 of the sensor module 100 enters a depth in tissue where a capillary blood field is encountered. The skin piercing member 110 stops at a capillary depth of about less than 3 mm below the skin surface and can reside for about less than 3 seconds to acquire a blood sample. The sample can be presented to the sensor module 100 by a rapid microfluidic flow initiated automatically by a combination of vascular blood pressure and capillary action. The sensor module 100 requires no other active mechanism to obtain a blood glucose value resulting in a passive system. Once the test is performed or completed, the carrier can be disposed by the user.

The elongated sensing component 142 has a length that extends along the lumen axis 10 and at least a section of the elongated sensing component 142 is positioned within the sample analysis zone 130. The elongated sensing component 142 can include sensing chemistry. In some examples, the sensing chemistry only covers the working electrode (WE) of the elongated sensing component 142. In other examples, the sensing chemistry covers additional portions of the elongated sensing component 142, including the reference electrode (RE). In an example, the sensing chemistry covers an entirety of the elongated sensing component 142.

The interaction of the skin piercing member 110 in concert with microfluidic forces (e.g., surface tension) within the lumen 144 promotes capillary flow of blood. Flow is initiated by ambient capillary pressure at the proximal lumen of the skin piercing member 110 when the piercing member is inserted into the papillary dermis to a depth of between 1-2 mm below the skin. Flow may also be promoted by the treatment of the lumen 144 with a surfactant compound. When so prepared, the combined factors create a driving mechanism to enable a spontaneous flow of capillary blood to enter the proximal lumen 144 and fill the skin piercing member 110 throughout its length.

The capillary stop 154 is formed at the skin piercing member 110 to inhibit the spontaneous blood flow from exiting the skin piercing member 110 at the distal end of the lumen 144. The self-limiting action of the flow into the interior passage of the skin piercing member 110 facilitates the lumen 144 to function as both an analysis cell 130—defined by the volume of the skin piercing member 110 and the length of the wetted working electrode portion residing within the skin piercing member 110—and as a counter electrode component of a multi electrode electrochemical cell.

The lumen 144 of the piercing member 110 may be sized appropriately to the configuration of the elongated sensing component 142 within it so as to optimize the microfluidic forces affecting the rate of transport thru the passage to the capillary stop 154. The lumen length must extend far enough above the tissue so as to provide sufficient surface area of the working electrode to produce a specified minimal output current. However, the lumen length may not be excessive or the time required to fill the lumen will increase with falling capillary pressure and fluid resistance slowing the transport rate.

The above described configuration of the electrode array within the piercing member 110 allows the major portion of the electrode surface to remain above the skin line presenting only the diameter of the piercing member 110 to the enervated tissue of the papillary dermis. This configuration allows the effective current produced by the electrode within the piercing member 110 to be two orders of magnitude larger than a traditional implanted sensor occupying the same footprint within tissue. In certain examples, the electrodes have an operational radius of less than 0.15 mm and a length of between 10 mm and 20 mm.

Referring to FIG. 2, a cross-sectional view of the skin piercing member 110 of the sensor module 100 is shown. In this example, the elongated sensing component 142 is positioned within the lumen 144 of the skin piercing member 110 and includes the elongated dielectric spacer 146 (e.g., a ribbon having a profiled transverse cross-sectional shape). The elongated dielectric spacer 146 can include the opposite first and second sides 147, 149. The working electrode 151 can be provided at the first side 147 and the reference electrode 153 can be provided at the second side 149. The working and reference electrodes can be coupled to and carried with the elongated dielectric spacer 146. The electrodes 151, 153 can include layers of electrically conductive material that have been applied (e.g., deposited, printed, disposed, placed, mounted, attached, etc.) to the first and second sides 147, 149 of the dielectric spacer 146.

The electrodes 151, 153 can include strips of electrically conductive material having lengths that extend along the length of the elongated dielectric spacer 146 and widths that extend partially across a corresponding width of the elongated dielectric spacer 146. In one example, the working electrode 151 includes a layer including gold and the reference electrode 153 includes a layer including Ag/AgCl. The elongated dielectric spacer 146 provides a spacing between the working and reference electrodes 151, 153 and prevents the working and reference electrodes 151, 153 from directly contacting one another. The elongated dielectric spacer 146 also maintains a spacing between the working and reference electrodes 151, 153 and the skin piercing member 110 to prevent direct contact between the electrodes 151, 153 and the skin piercing member 110. The elongated dielectric spacer 146 can have a transverse cross-sectional shape that is profiled to assist in maintaining a physical separation of the electrodes 151, 153 from the interior of the piercing member 110. For example, the transverse cross-sectional shape of the elongated dielectric spacer 146 can be profiled to assist in centering the elongated dielectric spacer 146 within the lumen of the skin piercing member 110. In one example, the transverse cross-sectional shape of the elongated dielectric spacer 146 has a flat middle section 155 and enlarged, rounded ends 157. In one example, the elongated dielectric spacer 146 includes a polymeric material such as medical grade polyetheretherketone. In certain examples, sensing chemistry of the type described herein (e.g., for sensing glucose) can be provided (e.g., printed) on the working electrode 151 and/or elsewhere on the elongated sensing component 142.

The sensor module 100 can become active when an ionic fluid, such as blood, fills the lumen 144 of the skin piercing member 110 and simultaneously contacts the interior of the skin piercing member 110, the working electrode 151, and the reference electrode 153. When the blood fills the lumen 144 of the skin piercing member 110, the sensing chemistry dissolves in the blood sample and is available for supporting and/or catalyzing the electrolysis of a selected analyte (e.g., glucose) within the blood sample at a predetermined potential applied between the working and counter electrodes. Blood within the lumen 144 of the skin piercing member 110 completes an electrical circuit through the fluid (i.e., the blood sample) between the working and counter electrodes. Once the circuit is established by a passive process of rapid capillary flow into the lumen 144 of the skin piercing member 110, blood continues up a defined open passage space (e.g., less than 0.004 inches circumferential clearance) surrounding the elongated sensing component 142 until encountering the capillary stop 154 feature formed at the base end 140 of the piercing member 110. The lumen 144 can be kept partially open at the base end 140 to serve as an air vent to promote the capillary flow.

In this example, the insertion end of the lumen 144 should be free of tissue plugs and reside at or below the vascular plexus (VP) between about 1 to 2 mm deep in the dermal layer where capillary vascular pressure is sufficient (about 14 to 22 mm Hg) to promote initial blood flow into a flow passage 128 of the skin piercing member 110, which is defined within the lumen 144 between the elongated sensing component 142 and the inner surface of the skin piercing member 110. Capillary flow can augment external vascular pressure to rapidly sweep up the interior of the flow passage 128 to the capillary stop 154. For example, the capillary flow can augment rapid, autonomous, and complete filling of the sample analysis zone 130. This filling can be co-determinant of response time and is promoted by the addition of surfactants such as, but not limited to, Triton materials to either the skin piercing member interior surface or to the detector chemistry or both.

Automation suitability can create a sensor configuration that will improve both quality of testing and the reliability of the test procedure for the consumer. The analysis zone method described can rely upon interdependent effects of defined part geometry, spatial relationships of components, and specific transitional properties of the enzyme detector chemistry as it is hydrated by the incoming blood matrix. These factors in concert with the dynamic interaction of blood flowing into the cell in response to vascular pressure and capillary action function as the analysis zone method for establishing a rapid and self-limiting amperometric assay cell formed along a defined section of a long fiber.

Flow up the lumen 144 of the skin piercing member 110 can be within the microfluidic domain of non-Newtonian laminar flow. This transport dynamic up the circumferential channel 128 defined within the lumen 144 between the elongated sensing component 142 and the inner surface of the skin piercing member 110 can be optimized by promoting low surface energy properties for the working electrode to allow complete and rapid wetting of the enzyme sensing chemistry. This surface property in turn can act in concert with the laminar flow dynamics to sweep the entire cavity containing the working electrode free of air pockets that could otherwise unpredictably affect the area of blood in contact with the electrode surface causing irreproducible sensor performance.

The capillary pressure, the viscosity of the blood media plus the surface energy interactions of the electrode coating and the skin piercing member 110 inner wall surface in concert with the distance separating the surfaces can all impact micro capillary flow characteristics.

The capillary stop 154 can be a mechanism that limits further fluid flow along the lumen 144 of the skin piercing member 110 and provides for venting of air displaced by the rapid filling of the capillary space by blood. In this example, one functional characteristic of the sensor is that the dry enzyme detector chemistry can be an effective insulator and can transition in phases from insulator to semiconductor to conductor as it becomes hydrated. This property prevents errant signal contributions to any portion of elongated sensing component 142 kept dry during the time of the glucose assay by defining the hydrated area of the elongated sensing component 142 through the combined use of the capillary stop 154 feature with mechanical control of the length of elongated sensing component 142 extending down into the skin piercing member passage 134. This also controls the surface area of the working electrode that is exposed to sample fluid. This method of defining electrode surface area provides for both manufacturing and functional advantages.

Referring again to FIGS. 10 and 11, the electrical contacts 112, 114 can be made of an electrically conductive material, such as, but not limited to, metals (i.e. copper, silver, aluminum, gold, bronze, and magnesium). During sample analysis at the sample analysis zone 130, a voltage can be applied between the working and counter electrodes. When the potential is applied, an electrical current will flow through the fluid sample to the working electrode. The current is a result of the oxidation or reduction of an analyte, such as glucose, in the volume of fluid sample located within the sample analysis zone. This electrochemical reaction occurs via the electron transfer agent in the enzyme sensing layer 152 and an optional electron transfer catalyst/enzyme in the enzyme sensing layer 152. By measuring the current flow generated at a given potential (e.g., with a controller described herein), the concentration of a given analyte (e.g., glucose) in the fluid sample can be determined. Those skilled in the art will recognize that current measurements can be obtained by a variety of techniques including, among other things, coulometric, potentiometric, perometric, voltometric, and other electrochemical techniques.

In this example, within a few hundredths of a second the defined sample analysis zone 130 is filled and the hydrating sensing chemistry initiates an exchange of electrons between the counter electrode (i.e., the skin piercing member 110) and the working electrode 151. A rising current appears at the data acquisition input of the sensor module 100 causing the software to start a countdown before initiating a data acquisition sequence for a prescribed number of discrete points (currently 500) taken at intervals over a set time window. The data set can be grouped by taking a mean of the discrete points. An area under the curve analysis can be applied to predict the plateau current for the sensor module 100. The correlation equates to a calibrated number representing a known glucose concentration at that current. The software then stores the value and can display it to the user on the meter LCD. The entire sequence from initiating actuator button to displayed blood glucose value requires less than 5 seconds. The result of the above testing sequence can be considered to be one reading. In certain examples, the modules 100 are single use and each can be used to provide one glucose reading. While the disclosure focuses primarily on glucose sensors, other analytes can be sensed as well by varying the sensing chemistry accordingly.

In certain embodiments, the data can be acquired using wireless device or portable electronic device (PED) such as, but not limited to, cellular phones. The PED can be used to act as a control unit for the sensor module 100. The sensor module 100 can be configured to interface with the PED which can store and display the glucose concentration to the user. In other embodiments, a separate test unit may be utilized to interface with a wireless device or PED (i.e., cellular phone). A chipset or similar component can be used in a glucose module to link to a PED via a broadband connection. The glucose test module can be connected automatically to the PED to initiate an application that would perform and display all the data management tasks. The glucose test module can be configured to have wide area network (WAN) capability to link to therapeutic software resident on other servers, such as, but not limited to, Cloud, that would completely automate the diabetics provisioning and treatment as well as link to a patient's physician or caregiver in real time. The glucose test module can be about 2.5 inch wide, about 3 inches long and about ¼ inch high.

FIG. 3 is a cross-sectional view of an alternative elongated sensing component 242 suitable for use in a sensor of the type described with respect to FIG. 2. For example, the component 242 can be positioned within a skin piercing member 110 in the same way described with respect to the elongated sensing component 142. The elongated sensing component 242 includes the elongated dielectric spacer 246. The elongated dielectric spacer 246 has a transverse cross-sectional shape that is generally in the shape of an X. Thus, the elongated dielectric spacer 246 can be described as having an X-shaped transverse profile. The X-shaped transverse profile defines the four pockets 247a-247d separated by the legs 249 of the X-shaped profile. Outer ends of the legs 249 are rounded and can be adapted for contacting an inner surface of the skin piercing member 110.

As depicted at FIG. 3, working and reference electrodes are positioned at opposite pockets of the spacer 246. For example, a working electrode 251 is shown at pocket 247a and a reference electrode 253 is shown at pocket 247c. Similar to the embodiment of FIG. 4, the working and reference electrodes 251, 253 can be coupled to and carried with the elongated dielectric spacer 246. Additionally, the electrodes 251, 253 can include layers of electrically conductive material that have been applied (e.g., printed) to the pockets 247a, 247c of the spacer 246. The electrodes 251, 253 can include strips of electrically conductive material having lengths that extend along the length of the elongated dielectric spacer 246 and widths that extend partially across corresponding widths of the pockets. In one example, the working electrode 251 includes a layer including gold and the reference electrode 253 includes a layer including silver/silver chloride.

The spacer 246 can be configured to assist in centering the spacer 246 within the lumen of the skin piercing member and to maintain physical separation between the electrodes 251, 253 and the interior of the skin piercing member 110. In one example, the spacer 246 includes a polymeric material such as medical grade polyetheretherketone. In certain examples, sensing chemistry 252 of the type described herein (e.g., for electrochemically sensing glucose) can be provided on the working electrode 251 and/or elsewhere on the elongated sensing component 242. In certain examples, additional electrodes can be applied to the pockets 247b and 247d. Such electrodes can be adapted for sensing oxygen or other types of biological analytes in addition to glucose (e.g., lactate) or can include a counter electrode. In still other examples, electrodes including conductive fibers or wires can be provided in the pockets 247a-247d. Such electrodes can include a polymeric monofilament covered with a conductive layer (e.g., a gold layer, a Ag/AgCl layer, etc.) and a sensing layer that may include enzyme chemistry, mediator chemistry, glucose sensing chemistry such as glucose oxidase or glucose dehydrogenase or other chemistry. Example conductive fibers and wires are disclosed at PCT International Publication No. WO 2014/089058, which is hereby incorporated by reference in its entirety.

In certain examples, the spacer 246 can be moved from an expanded orientation (see FIG. 3) to a flattened orientation (see FIG. 4) during application of the electrodes. By flattening the spacer 246, larger dimensions D can be provided between edges of the electrodes and outer edges of the spacer 246. In this way, material being applied during the electrode application process is prevented from inadvertently being applied to an adjacent pocket or elsewhere on the spacer 246 where it is not desired to provide the electrode material.

FIG. 5 shows another elongated electric spacer 446 that can be used to form an elongated sensing component of the type described with respect to FIG. 2. The elongated dielectric spacer 446 has a transverse cross-sectional shape configured to define two separate pockets 447a, 447b that are separated from one another by an intermediate leg 448 and that have open sides 449a, 449b that face in the same direction. The spacer 446 also includes exterior legs 450 that cooperate with the central leg 448 to define the pockets 447a, 447b. The legs 448, 450 have rounded and enlarged ends 452 that can assist in retaining electrodes within the pockets 447a, 447b and also can assist in maintaining separation between the electrodes and the interior surface of the skin piercing member. In certain examples, the pockets 447a, 447b are configured to hold working and reference electrodes that can include fibers or wires of the type described by PCT International Publication No. WO 2014/089058. In still other embodiments, working and reference electrodes can include metal layers applied (e.g., printed) directly to the spacer 446 surface within the pockets 447a, 447b. In this example, multiple electrodes can be printed on one side of the spacer 446.

FIG. 6 shows still another elongated dielectric spacer 546 suitable for use in a sensor of the type described with respect to FIG. 2. For example, the elongated spacer 546 can be positioned within a skin piercing member 110 in the same way described with respect to the elongated dielectric spacer 146. As depicted at FIG. 6, the elongated dielectric spacer 546 has a transverse cross-sectional shape that includes two separate pockets 547a, 547b. The pockets 547a, 547b are separated by a central region 549 and are defined between flexible legs 550. The pockets 547a, 547b have insides 551a, 551b that face in opposite directions from one another. In certain examples, electrodes such as working and reference electrodes can be positioned at the pockets 547a, 547b. In certain examples, the electrodes can include fibers or wires of the type described by PCT International Publication No. WO 2014/089058. In still other embodiments, the electrodes can be formed by applying (e.g., printing) conductive material to the surface of the dielectric spacer 546 within the pockets 547a, 547b.

FIG. 7 shows still another elongated dielectric spacer 646 that can be used in place of the elongated dielectric spacer 146 described with respect to FIG. 2. Similar to the previously described examples, elongated dielectric spacer 646 can be positioned within the lumen of the skin piercing member 110 and can form part of an elongated sensing component that also includes a plurality of electrodes. In certain examples, electrodes can include conductive fibers or wires of the type described by PCT International Publication No. WO 2014/089058. Such conductive wires or fibers can be contained or captured within the pockets 647a-647d of the spacer 646. In other examples, the electrodes can be formed by applying (e.g., printing) conductive layers to the dielectric spacer 646 within the pockets 647a-647d. In certain examples, the electrodes can include a working electrode, a reference electrode, and a supplemental electrode. The supplemental electrode may be employed as a comparison means to determine what portion of a raw sensor current comes from interferent components, such as vitamin C, rather than a desired analyte, such as glucose. In other examples, the working electrodes can include electrodes suitable for detecting different analytes (e.g., glucose and lactate) within the blood sample. In still other examples, one of the electrodes can be used to detect oxygen concentrations within the blood sample or can include a counter electrode.

Figure 13:
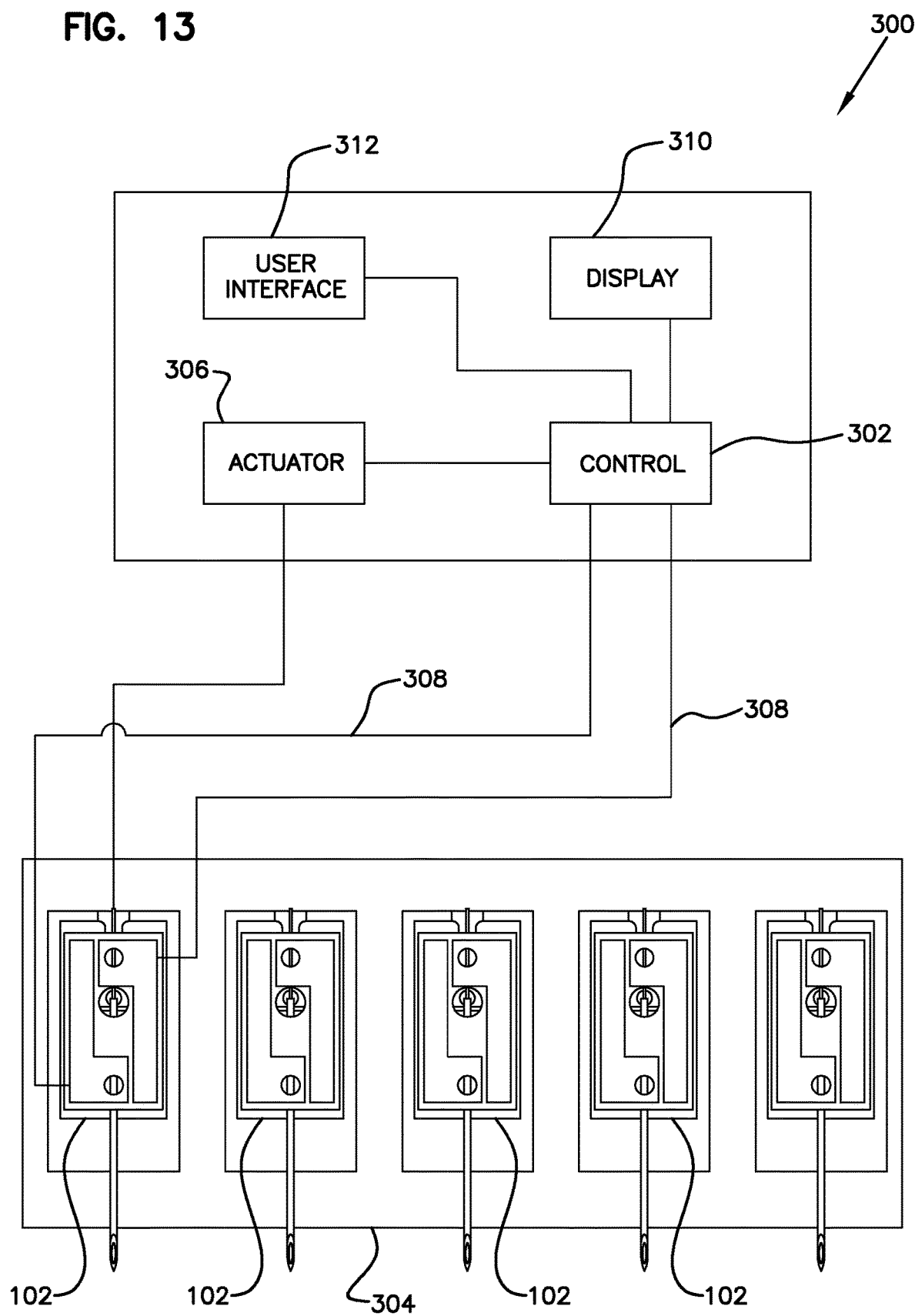
FIG. 13 is a schematic view of a sensing unit in accordance with the principles of the present disclosure that incorporates a plurality of the sensing modules of FIG. 10.

Referring to FIG. 13, a schematic of an analyte monitoring unit 300 is shown. The unit 300 where the modules 100 may be arrayed within a cartridge designed to provide a supply of multiple sensors that may be directly positioned on the skin of a patient's forearm or fingertip in order to obtain a blood glucose concentration. It will be appreciated that one or more sensor modules 100 can be incorporated as subcomponents into an analyte monitoring unit 300. The unit 300 includes a controller 302 that couples to a module holder 304. The module holder 304 is configured to hold one or more sensor modules 100. Each sensor module 100 is configured to obtain one or more fluid samples, to measure a concentration level for one or more analytes (e.g., glucose, lactate, etc.), and to generate a signal (e.g., an electrical signal) indicating the concentration level. For example, the module holder 304 shown in FIG. 12 contains five sensor modules 100. In one embodiment, each sensor module 100 is configured to analyze a single fluid sample. In such an embodiment, the sensor module 100 can be removed from the module holder 304 after one use. In other embodiments, each sensor module 100 can be configured to analyze a greater number of fluid samples.

In general, the unit 300 includes a controller 302, an actuator 306, and input lines 308. The controller 302 controls the actuator 306 for driving the skin piercing members 110 of each sensor module 100 between the extended and retracted positions to obtain a fluid sample. The controller 302 can include a microcontroller, a mechanical controller, software driven controller, a hardware driven controller, a firmware driven controller, etc. The controller can include a microprocessor that interfaces with memory.

The controller 302 instructs the actuator 306 when to operate the sensor module 100 to obtain a fluid sample for analysis. The controller 302 also can instruct the module holder 304 and/or the actuator 306 to eject the used sensor module 100.

The input lines 308 carry the data/signals/readings (e.g., voltage values) generated at the elongated working electrode 142 of the sensor module 100 during analysis of a fluid sample to the controller 302 for analysis. The controller 302 converts the signals to an analyte concentration level (e.g., a blood glucose reading) or other desired information. The controller 302 causes the display 310 to indicate the processed information to the user. Other information also can be presented on the display 310. In one embodiment, the display 310 is a visual display. In other embodiments, an audio display also can be used. Additional information can be provided to the controller 302 via a user interface 312 (e.g., buttons, switches, etc.).

One aspect of the present disclosure relates to a sensor module that includes a carrier and a skin piecing member carried by the carrier. The skin piercing member has a skin piecing end positioned opposite from a base end. In certain examples, the skin piercing member has a construction that is electrically conductive (e.g., stainless steel) and the skin piercing member functions as a counter electrode. In certain examples, the skin piecing is relatively small in diameter (e.g., 31-28 gauge or smaller in diameter). The skin piecing member defines a lumen that extends along the central longitudinal axis from the skin piercing end toward the base end where the lumen has a lumen axis. The sensor module includes a blood sample analysis zone located entirely within the lumen of the skin piercing member and a capillary flow stop for stopping capillary flow at a predetermined location within the lumen of the skin piercing member. The sensor module further includes an elongated sensing component positioned within the lumen. The sensing component has a length that extends along the lumen axis where at least a section of a working electrode is positioned within the analysis zone and the working electrode includes sensing chemistry. In certain examples, the sensor module includes a three electrode sensing system including a counter electrode formed by the skin piecing member and working and reference electrodes associated with the sensing component. In certain examples, the sensing component includes an elongated insulator (e.g., an elongated polymeric extrusion, an elongated polymeric substrate, an elongated polymeric member, an elongated dielectric holder, an elongated spacer, etc.) for supporting, holding, containing. In certain examples, the elongated insulator functions as a spacer for preventing working and reference electrodes from making direct electrical contact with the skin piecing member/counter electrode. In certain examples, the elongated insulator includes a medical grade polymer such as medical grade polyetheretherketone (PEEK). In certain examples, the working and reference electrodes include electrically conductive fibers or wires, and the elongated insulator includes pockets for receiving and holding the fibers or wires. In certain examples, the elongated insulator functions as a substrate, and the working and reference electrodes includes conductive layers that are supported by the elongated insulator and prevented from making direct electrical contact with one another by the elongated insulator. In certain examples, the working and reference electrodes are coated, printed, deposited or otherwise applied on the elongated insulator. In certain examples, the working electrode can include a layer of gold and a layer of sensing chemistry. In certain examples, the sensing chemistry can include a redox mediator and a redox enzyme (e.g., glucose oxidase or glucose dehydrogenase). In certain examples, the reference electrode can include a layer of silver/silver chloride (Ag/AgCl). In certain examples, the skin piercing member does not function as a counter electrode, and the working, counter and reference electrodes of the three electrode sensing system are printed on the elongated insulator positioned within the lumen of the skin piercing member. In some examples, the elongated insulator can be a micro extrusion. In some examples, the elongated insulator can have a ribbon shaped transverse cross-sectional profile.

Another aspect of the present disclosure relates to a sensor module including a carrier and a skin piecing member carried by the carrier. The skin piercing member has a skin piecing end positioned opposite from a base end. The skin piecing member defines a lumen that extends along the central longitudinal axis from the skin piercing end toward the base end and the lumen defines a lumen axis. The sensor module includes a blood sample analysis zone located within the lumen of the skin piercing member and elongated working and reference electrodes positioned within the lumen. The working and reference electrodes have lengths that extend along the lumen axis, at least a section of the working and reference electrodes being positioned within the analysis zone. The working electrode can include sensing chemistry. The sensor module can include a 3 electrode sensing system with the skin piercing member functioning as a counter electrode and with the working and reference electrodes being positioned within the skin piercing member. A dielectric insulator can prevent direct electrical contact between the working electrode, the reference electrode and the counter electrode. The dielectric insulator can be a polymeric extrusion having a predetermined transverse cross-sectional shape/profile configured to maintain spacing between the counter electrode, the working electrode and the reference electrode. The working and reference electrodes can have has ends within 0.5 millimeters of a tip of the skin piercing member. In other examples, the skin piercing member does not function as a counter electrode, and the working, counter and reference electrodes of the three electrode sensing system are printed on the dielectric insulator positioned within the lumen of the skin piercing member. In still another example, the skin piercing member functions as a counter electrode but does not function as a combined reference/counter electrode.

A further aspect of the present disclosure relates to a sensor module including a carrier movable relative to a base between a first position and second position and a skin piecing member carried by the carrier. The skin piercing member has a skin piecing end positioned opposite from a base end and the skin piercing member defines a lumen that extends along the central longitudinal axis from the skin piercing end toward the base end. The lumen defines a lumen axis. The sensor module includes a blood sample analysis zone located within the lumen (e.g., in some examples entirely within the lumen) of the skin piercing member and an elongated working electrode positioned within the lumen. The working electrode has a length that extends along the lumen axis where at least a section of the working electrode is positioned within the analysis zone and the working electrode has sensing chemistry. In certain examples, the skin piecing member is a counter electrode and a separate reference electrode is positioned within the analysis zone along with the working electrode. In other examples, the skin piercing member does not function as a counter electrode, and the working, counter and reference electrodes of the three electrode sensing system are printed on an elongate dielectric insulator (e.g., a micro extrusion) positioned within the lumen of the skin piercing member.

A further aspect of the present disclosure relates to a sensor module that includes a carrier and a skin piercing member carried by the carrier. The skin piercing member has a skin piercing end positioned opposite from a base end and the skin piercing member defines a lumen that extends along the central longitudinal axis from the skin piercing end toward the base end. The lumen defines a lumen axis. The sensor module includes a blood sample analysis zone located within the lumen of the skin piercing member and an elongated working electrode positioned within the lumen. The working electrode has a length that extends along the lumen axis where at least a section of the working electrode is positioned within the analysis zone. The working electrode can include sensing chemistry on a wire or fiber that is at least partially electrically conductive. The working electrode can also include an electrically conductive layer provided on an elongated dielectric member. The electrically conductive layer can include gold and can be covered with a sensing chemistry. In certain examples, a reference electrode can also be provided on the elongated dielectric member. In certain examples, the skin pierce member is or includes a counter electrode. In other examples, the working, counter and reference electrodes are printed along the length of the elongated dielectric member.

A further aspect of the present disclosure relates to a method for taking a blood analyte reading that includes puncturing skin with a skin piercing member having a lumen and positioning a tip of the skin piercing member in a capillary blood field less than 3 millimeters beneath the skin. The method includes initiating blood flow into the lumen by a combination of vascular blood pressure and capillary action to passively bring a blood sample to an analysis zone entirely within the lumen and sensing the blood analyte in the analysis zone. The method also includes using the skin piercing member as a counter electrode and providing working and reference electrodes within the analysis zone. In another example, the working, counter and reference electrodes are printed along the length of an elongated dielectric member that extends through the lumen along the analysis zone.

Still another aspect of the present disclosure relates to a device for sensing an analyte in a blood sample. The device includes an elongated working electrode having a first portion that is subcutaneous during testing and a second portion that extends outside the body during testing. The working electrode can be supported by an elongated insulator that also supports a reference electrode. The working and reference electrodes can include conductive layers supported on fibers or wires supported by the elongated insulator, or can include conductive layers applied to the elongated insulator. The working and reference electrodes can be contained within a skin piercing member that also functions as a counter electrode. The device is configured for a one time use in which one analyte reading is taken. In another example, the working, counter and reference electrodes are printed along the length of the elongated insulator.

Still another aspect of the present disclosure relates to a device for sensing an analyte in a blood sample. The device includes an elongated working electrode having a first conductive portion that is subcutaneous during testing and a second conductive portion that extends outside the body during testing. The working electrode can include a layer of sensing chemistry on the first and second conductive portions. The device further includes a skin piercing member having a lumen in which the working electrode is positioned. The device is configured such that a blood analysis zone of the device fills passively. In one example, the skin piercing member can function as a counter electrode. The working electrode and a separate reference electrode can be provided within the skin piercing member. In some examples, at least one of the electrodes is printed along the length of an elongated dielectric insulator (e.g., a micro extrusion) positioned within the lumen of the skin piercing member. In one example, the working, counter and reference electrodes are printed along the length of the elongated dielectric insulator. In one example, the working and reference electrodes are printed along the length of the dielectric insulator.

From the forgoing detailed description, it will be evident that modifications and variations can be made without departing from the spirit and scope of the disclosure.

What is claimed is:
1. A sensor comprising:
   a skin piercing member having a skin piercing end positioned opposite from a base end, the skin piercing member defining a lumen that extends along a lumen axis from the skin piercing end toward the base end;
   a blood sample analysis zone located within the lumen of the skin piercing member; and an elongated sensing component positioned within the lumen, the elongated sensing component including elongated working and reference electrodes printed on an elongated spacer having a length that extends along the lumen axis, at least a section of each of the working and reference electrodes being positioned within the analysis zone, the elongated spacer having a transverse cross-sectional shape including a flat middle portion and ball-shaped ends each having a larger thickness than the flat middle portion.

2. The sensor of claim 1, further including a counter electrode defined by the skin piercing member.

3. The sensor of claim 2, wherein the counter electrode is not a combined reference/counter electrode.

4. The sensor of claim 1, wherein the working electrode is an aerosol jet printed electrode.

5. The sensor of claim 4, wherein the reference electrode is an aerosol jet printed electrode.

6. The sensor of claim 1, wherein the elongated sensing component includes aerosol jet printed sensing chemistry.

7. The sensor of claim 6, wherein the aerosol jet printed sensing chemistry covers the working electrode.

8. The sensor of claim 7, wherein the aerosol jet printed sensing chemistry covers the reference electrode.

9. The sensor of claim 1, wherein the working electrode and the reference electrode are printed on one side of the elongated spacer.

10. The sensor of claim 1, wherein the working electrode, the reference electrode and a counter electrode are printed on the elongated spacer.

11. The sensor of claim 10, wherein the working electrode, the reference electrode and the counter electrode are printed on one side of the elongated spacer.

12. The sensor of claim 1, wherein the working and reference electrodes are printed on opposite sides of the flat middle portion.

13. The sensor of claim 1, wherein the working electrode, the reference electrode and a counter electrode are printed on one side of the flat middle portion.

14. The sensor of claim 1, wherein the skin piercing member defines a capillary flow stop and also includes a vent.

15. The sensor of claim 1, wherein the working electrode is printed on a first side of the elongated spacer and the reference electrode is printed on an opposite second side of the elongated spacer.

16. The sensor of claim 1, wherein the working electrode includes electrically conductive particles of micrometer or nanometer size deposited on the elongated spacer.

17. The sensor of claim 1, wherein the working electrode has a honeycomb pattern and the sensing chemistry is disposed within cells of the honeycomb pattern.

18. The sensor of claim 17, wherein a diffusive membrane or coating is disposed over the working electrode to cover the sensing chemistry within the cells.

19. A sensor comprising:
a skin piercing member having a skin piercing end positioned opposite from a base end, the skin piercing member defining a lumen that extends along a lumen axis from the skin piercing end toward the base end;
a blood sample analysis zone located within the lumen of the skin piercing member; and
an elongated sensing component positioned within the lumen, the elongated sensing component including elongated working and reference electrodes applied to an elongated spacer having a length that extends along the lumen axis, at least a section of each of the working and reference electrodes being positioned within the analysis zone, and wherein the elongated spacer is a ribbon having a profiled transverse cross-sectional shape that includes a flat middle portion and enlarged, rounded ends, the profiled transverse cross-sectional shape being symmetrical about an axis perpendicular to the length of the elongated spacer.

20. The sensor of claim 19, wherein the working and reference electrodes are printed on opposite sides of the flat middle portion.

21. The sensor of claim 19, wherein the working electrode, the reference electrode and a counter electrode are printed on one side of the flat middle portion.

* * * * *